(12) United States Patent
Hall et al.

(10) Patent No.: US 7,810,692 B2
(45) Date of Patent: Oct. 12, 2010

(54) DISPOSABLE LOADING UNIT WITH FIRING INDICATOR

(75) Inventors: Steven G. Hall, Cincinnati, OH (US);
Randall J. Tanguay, Lebanon, OH (US); Jeffrey D. Messerly, Cincinnati, OH (US); Galen C. Robertson, Cincinnati, OH (US); Andrew M. Zwolinski, Cincinnati, OH (US); Frederick E. Shelton, IV, Hillsboro, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 255 days.

(21) Appl. No.: 12/031,618

(22) Filed: Feb. 14, 2008

(65) Prior Publication Data

US 2009/0206135 A1 Aug. 20, 2009

(51) Int. Cl.
*A65B 17/065* (2006.01)
(52) U.S. Cl. .................... 227/176.1; 227/19; 227/175.2
(58) Field of Classification Search .................... 227/19, 227/176.1, 175.1, 175.2, 180.1; 606/139, 606/219
See application file for complete search history.

(56) References Cited

U.S. PATENT DOCUMENTS

| | | | |
|---|---|---|---|
| 3,490,675 A | 1/1970 | Green et al. |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |

(Continued)

FOREIGN PATENT DOCUMENTS

CA 2458946 A1 3/2003

(Continued)

OTHER PUBLICATIONS

European Search Report, Application 09250365.5, dated Jun. 9, 2009 (8 pages).

(Continued)

*Primary Examiner*—Scott A. Smith

(57) ABSTRACT

A disposable loading unit for operable attachment to a surgical stapling apparatus. The disposable loading unit may have a carrier that supports a staple cartridge therein, an anvil assembly that is movably coupled to the carrier, and an axial drive assembly that is constructed to move in a distal direction from a start position to an end position through the staple cartridge in response to a drive motion imparted to the axial drive assembly from the surgical stapling apparatus. A firing indicator is provided on at least one of the anvil assembly and housing for indicating a position of the axial drive assembly as the axial drive assembly is driven from the start position to the end position.

17 Claims, 30 Drawing Sheets

U.S. PATENT DOCUMENTS

| | | | |
|---|---|---|---|
| 4,522,327 A | 6/1985 | Korthoff et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,610,383 A | 9/1986 | Rothfuss et al. | |
| 4,629,107 A | 12/1986 | Fedotov et al. | |
| 4,655,222 A | 4/1987 | Florez et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,752,024 A | 6/1988 | Green et al. | |
| 4,754,909 A | 7/1988 | Barker et al. | |
| 4,767,044 A | 8/1988 | Green | |
| 4,805,823 A | 2/1989 | Rothfuss | |
| 4,807,628 A | 2/1989 | Peters et al. | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,869,414 A | 9/1989 | Green et al. | |
| 4,869,415 A | 9/1989 | Fox | |
| 4,941,623 A | 7/1990 | Pruitt | |
| 4,944,443 A | 7/1990 | Oddsen et al. | |
| 5,065,929 A | 11/1991 | Schulze et al. | |
| 5,071,430 A | 12/1991 | de Salis et al. | |
| 5,129,570 A | 7/1992 | Schulze et al. | |
| 5,137,198 A | 8/1992 | Nobis et al. | |
| 5,139,513 A | 8/1992 | Segato | |
| 5,158,567 A | 10/1992 | Green | |
| 5,211,649 A | 5/1993 | Kohler et al. | |
| 5,221,036 A | 6/1993 | Takase | |
| 5,222,975 A | 6/1993 | Crainich | |
| 5,258,009 A | 11/1993 | Conners | |
| 5,282,806 A | 2/1994 | Haber et al. | |
| 5,282,829 A | 2/1994 | Hermes | |
| 5,304,204 A | 4/1994 | Bregen | |
| 5,342,395 A | 8/1994 | Jarrett et al. | |
| 5,342,396 A | 8/1994 | Cook | |
| 5,350,400 A | 9/1994 | Esposito et al. | |
| 5,352,235 A | 10/1994 | Koros et al. | |
| 5,366,479 A | 11/1994 | McGarry et al. | |
| 5,383,895 A | 1/1995 | Holmes et al. | |
| 5,397,324 A | 3/1995 | Carroll et al. | |
| 5,417,361 A | 5/1995 | Williamson, IV | |
| 5,425,745 A | 6/1995 | Green et al. | |
| 5,474,566 A | 12/1995 | Alesi et al. | |
| 5,478,354 A | 12/1995 | Tovey et al. | |
| 5,480,089 A | 1/1996 | Blewett | |
| 5,484,451 A | 1/1996 | Akopov et al. | |
| 5,485,947 A | 1/1996 | Olson et al. | |
| 5,487,499 A | 1/1996 | Sorrentino et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,547,117 A | 8/1996 | Hamblin et al. | |
| 5,553,765 A | 9/1996 | Knodel et al. | |
| 5,554,169 A | 9/1996 | Green et al. | |
| 5,560,530 A * | 10/1996 | Bolanos et al. | 227/176.1 |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,571,116 A | 11/1996 | Bolanos et al. | |
| 5,575,799 A | 11/1996 | Bolanos et al. | |
| 5,577,654 A | 11/1996 | Bishop | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,624,452 A | 4/1997 | Yates | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,645,209 A | 7/1997 | Green et al. | |
| 5,647,526 A | 7/1997 | Green et al. | |
| 5,649,937 A | 7/1997 | Bito et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,527 A | 9/1997 | Cook | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,690,269 A | 11/1997 | Bolanos et al. | |
| 5,692,668 A | 12/1997 | Schulze et al. | |
| 5,697,543 A | 12/1997 | Burdorff | |
| 5,702,408 A | 12/1997 | Wales et al. | |
| 5,704,534 A | 1/1998 | Huitema et al. | |
| 5,706,997 A | 1/1998 | Green et al. | |
| 5,711,472 A | 1/1998 | Bryan | |
| 5,715,987 A | 2/1998 | Kelley et al. | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,728,121 A | 3/1998 | Bimbo et al. | |
| 5,730,758 A | 3/1998 | Allgeyer | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A * | 7/1998 | Mastri et al. | 227/175.3 |
| 5,782,397 A | 7/1998 | Koukline | |
| 5,785,232 A | 7/1998 | Vidal et al. | |
| 5,794,834 A | 8/1998 | Hamblin et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,820,009 A | 10/1998 | Melling et al. | |
| 5,826,776 A | 10/1998 | Schulze et al. | |
| 5,833,695 A | 11/1998 | Yoon | |
| 5,836,503 A | 11/1998 | Ehrenfels et al. | |
| 5,839,639 A | 11/1998 | Sauer et al. | |

| | | |
|---|---|---|
| 5,855,311 A | 1/1999 | Hamblin et al. |
| 5,865,361 A | 2/1999 | Milliman et al. |
| 5,868,760 A | 2/1999 | McGuckin, Jr. |
| 5,878,937 A | 3/1999 | Green et al. |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,919,198 A | 7/1999 | Graves, Jr. et al. |
| 5,941,442 A | 8/1999 | Geiste et al. |
| 5,951,574 A | 9/1999 | Stefanchik et al. |
| 5,954,259 A | 9/1999 | Viola et al. |
| 6,010,054 A | 1/2000 | Johnson et al. |
| 6,032,849 A | 3/2000 | Mastri et al. |
| 6,045,560 A | 4/2000 | McKean et al. |
| 6,050,472 A | 4/2000 | Shibata |
| 6,079,606 A | 6/2000 | Milliman et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,155,473 A | 12/2000 | Tompkins et al. |
| 6,168,605 B1 | 1/2001 | Measamer et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,387,113 B1 | 5/2002 | Hawkins et al. |
| 6,406,440 B1 | 6/2002 | Stefanchik |
| RE37,814 E | 8/2002 | Allgeyer |
| 6,436,107 B1 | 8/2002 | Wang et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,988 B2 | 10/2003 | Weadock |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,730 B2 | 10/2008 | Viola |
| 7,434,715 B2 | 10/2008 | Shelton, IV et al. |
| 7,438,209 B1 | 10/2008 | Hess et al. |
| 7,441,685 B1 | 10/2008 | Boudreaux |
| 7,464,847 B2 | 12/2008 | Viola et al. |
| 7,481,347 B2 | 1/2009 | Roy |
| 7,490,749 B2 | 2/2009 | Schall et al. |
| 7,494,039 B2 | 2/2009 | Racenet et al. |

| | | |
|---|---|---|
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,631,793 B2 | 12/2009 | Rethy et al. |
| 7,665,646 B2 | 2/2010 | Prommersberger |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0180634 A1 | 8/2006 | Shelton, IV et al. |
| 2006/0226196 A1 | 10/2006 | Hueil et al. |
| 2006/0241692 A1 | 10/2006 | McGuckin et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0045379 A1 | 3/2007 | Shelton, IV |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |

| | | | | | | |
|---|---|---|---|---|---|---|
| 2009/0001125 A1 | 1/2009 | Hess et al. | | EP | 0630612 A1 | 12/1994 |
| 2009/0001126 A1 | 1/2009 | Hess et al. | | EP | 0634144 A1 | 1/1995 |
| 2009/0001128 A1 | 1/2009 | Weisenburgh, II et al. | | EP | 0646356 A2 | 4/1995 |
| 2009/0001130 A1 | 1/2009 | Hess et al. | | EP | 0646357 A1 | 4/1995 |
| 2009/0005807 A1 | 1/2009 | Hess et al. | | EP | 0653189 A2 | 5/1995 |
| 2009/0005808 A1 | 1/2009 | Hess et al. | | EP | 0669104 A1 | 8/1995 |
| 2009/0005809 A1 | 1/2009 | Hess et al. | | EP | 0511470 B1 | 10/1995 |
| 2009/0012556 A1 | 1/2009 | Boudreaux et al. | | EP | 0679367 A2 | 11/1995 |
| 2009/0076534 A1 | 3/2009 | Shelton, IV et al. | | EP | 0392547 B1 | 12/1995 |
| 2009/0090763 A1 | 4/2009 | Zemlok et al. | | EP | 0685204 A1 | 12/1995 |
| 2009/0200355 A1 | 8/2009 | Baxter, III et al. | | EP | 0699418 A1 | 3/1996 |
| 2009/0206123 A1 | 8/2009 | Doll et al. | | EP | 0702937 A1 | 3/1996 |
| 2009/0206124 A1 | 8/2009 | Hall et al. | | EP | 0705571 A1 | 4/1996 |
| 2009/0206125 A1 | 8/2009 | Huitema et al. | | EP | 0484677 B2 | 6/1996 |
| 2009/0206126 A1 | 8/2009 | Huitema et al. | | EP | 0541987 B1 | 7/1996 |
| 2009/0206128 A1 | 8/2009 | Hueil et al. | | EP | 0667119 B1 | 7/1996 |
| 2009/0206129 A1 | 8/2009 | Doll et al. | | EP | 0770355 A1 | 5/1997 |
| 2009/0206130 A1 | 8/2009 | Hall et al. | | EP | 0503662 B1 | 6/1997 |
| 2009/0206131 A1 | 8/2009 | Weisenburgh, II et al. | | EP | 0578425 B1 | 9/1997 |
| 2009/0206132 A1 | 8/2009 | Hueil et al. | | EP | 0625335 B1 | 11/1997 |
| 2009/0206133 A1 | 8/2009 | Morgan et al. | | EP | 0552423 B1 | 1/1998 |
| 2009/0206134 A1 | 8/2009 | Swayze et al. | | EP | 0592244 B1 | 1/1998 |
| 2009/0206136 A1 | 8/2009 | Moore et al. | | EP | 0648476 B1 | 1/1998 |
| 2009/0206137 A1 | 8/2009 | Hall et al. | | EP | 0676173 B1 | 9/1998 |
| 2009/0206138 A1 | 8/2009 | Smith et al. | | EP | 0603472 B1 | 11/1998 |
| 2009/0206139 A1 | 8/2009 | Hall et al. | | EP | 0605351 B1 | 11/1998 |
| 2009/0206140 A1 | 8/2009 | Scheib et al. | | EP | 0878169 A1 | 11/1998 |
| 2009/0206141 A1 | 8/2009 | Huitema et al. | | EP | 0879742 A1 | 11/1998 |
| 2009/0206142 A1 | 8/2009 | Huitema et al. | | EP | 0760230 B1 | 2/1999 |
| 2009/0206143 A1 | 8/2009 | Huitema et al. | | EP | 0537572 B1 | 6/1999 |
| 2009/0206144 A1 | 8/2009 | Doll et al. | | EP | 0552050 B1 | 5/2000 |
| 2009/0209946 A1 | 8/2009 | Swayze et al. | | EP | 1090592 A1 | 4/2001 |
| 2009/0218384 A1 | 9/2009 | Aranyi | | EP | 1256318 B1 | 5/2001 |
| 2009/0242610 A1 | 10/2009 | Shelton, IV et al. | | EP | 0908152 B1 | 1/2002 |
| 2009/0255974 A1 | 10/2009 | Viola | | EP | 0872213 B1 | 5/2002 |
| 2009/0255978 A1 | 10/2009 | Viola et al. | | EP | 1238634 A2 | 9/2002 |
| 2009/0289096 A1 | 11/2009 | Shelton, IV et al. | | EP | 0656188 B1 | 1/2003 |
| 2010/0032470 A1 | 2/2010 | Hess et al. | | EP | 0829235 B1 | 6/2003 |
| 2010/0065605 A1 | 3/2010 | Shelton, VI et al. | | EP | 0813843 B1 | 10/2003 |
| 2010/0065609 A1 | 3/2010 | Schwemberger | | EP | 0741996 B1 | 2/2004 |
| 2010/0069942 A1 | 3/2010 | Shelton, IV | | EP | 0705570 B1 | 4/2004 |
| 2010/0072251 A1 | 3/2010 | Baxter, III et al. | | EP | 1086713 B1 | 5/2004 |
| 2010/0072252 A1 | 3/2010 | Baxter, III et al. | | EP | 1426012 A1 | 6/2004 |
| 2010/0072253 A1 | 3/2010 | Baxter, III et al. | | EP | 0888749 B1 | 9/2004 |
| 2010/0072256 A1 | 3/2010 | Baxter, III et al. | | EP | 1477119 A1 | 11/2004 |
| 2010/0076474 A1 | 3/2010 | Yates et al. | | EP | 1479345 A1 | 11/2004 |
| 2010/0076475 A1 | 3/2010 | Yates et al. | | EP | 1479347 A1 | 11/2004 |
| 2010/0089970 A1 | 4/2010 | Smith et al. | | EP | 1479348 A1 | 11/2004 |
| 2010/0089974 A1 | 4/2010 | Shelton, IV | | EP | 1520521 A1 | 4/2005 |
| 2010/0096435 A1 | 4/2010 | Fuchs et al. | | EP | 1520523 A1 | 4/2005 |
| 2010/0133317 A1 | 6/2010 | Shelton, IV et al. | | EP | 1520525 A1 | 4/2005 |
| 2010/0133318 A1 | 6/2010 | Boudreaux | | EP | 1522264 A1 | 4/2005 |
| | | | | EP | 1550408 A1 | 7/2005 |
| FOREIGN PATENT DOCUMENTS | | | | EP | 1557129 A1 | 7/2005 |
| CA | 2512960 A1 | 1/2006 | | EP | 1064883 B1 | 8/2005 |
| CA | 2514274 A1 | 1/2006 | | EP | 1157666 B1 | 9/2005 |
| DE | 273689 C | 5/1914 | | EP | 1621138 A2 | 2/2006 |
| DE | 1775926 A | 1/1972 | | EP | 1621139 A2 | 2/2006 |
| DE | 9412228 U | 9/1994 | | EP | 1621141 A2 | 2/2006 |
| DE | 19924311 A1 | 11/2000 | | EP | 1621145 A2 | 2/2006 |
| DE | 69328576 T2 | 1/2001 | | EP | 1652481 A2 | 5/2006 |
| DE | 20112837 U1 | 10/2001 | | EP | 1382303 B1 | 6/2006 |
| DE | 20121753 U1 | 4/2003 | | EP | 1045672 B1 | 8/2006 |
| DE | 10314072 A1 | 10/2004 | | EP | 1617768 B1 | 8/2006 |
| EP | 0122046 A1 | 10/1984 | | EP | 1702567 A2 | 9/2006 |
| EP | 0070230 B1 | 10/1985 | | EP | 1129665 B1 | 11/2006 |
| EP | 0033548 B1 | 5/1986 | | EP | 1256317 B1 | 12/2006 |
| EP | 0276104 A2 | 7/1988 | | EP | 1728473 A1 | 12/2006 |
| EP | 0639349 A2 | 2/1994 | | EP | 1728475 A2 | 12/2006 |
| EP | 0324636 B1 | 3/1994 | | EP | 1479346 B1 | 1/2007 |
| EP | 0593920 A1 | 4/1994 | | EP | 1484024 A1 | 1/2007 |
| EP | 0600182 A2 | 6/1994 | | EP | 1754445 A2 | 2/2007 |
| | | | | EP | 1759812 A1 | 3/2007 |

| | | | |
|---|---|---|---|
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A2 | 8/2007 |
| EP | 1813209 A1 | 8/2007 |
| EP | 1839596 A1 | 10/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A1 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

U.S. Appl. No. 12/031,624, filed Feb. 14, 2008.
Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

* cited by examiner

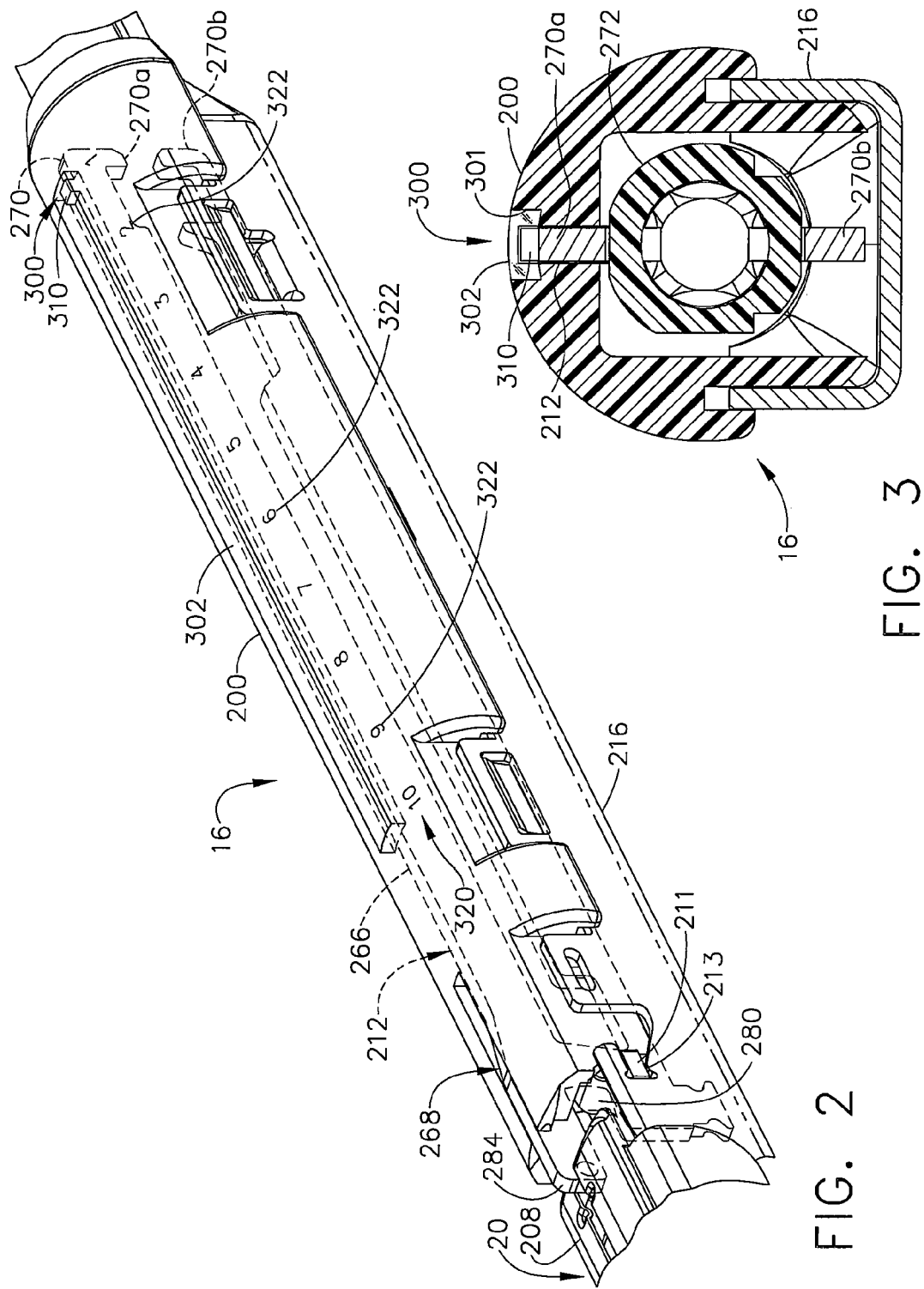

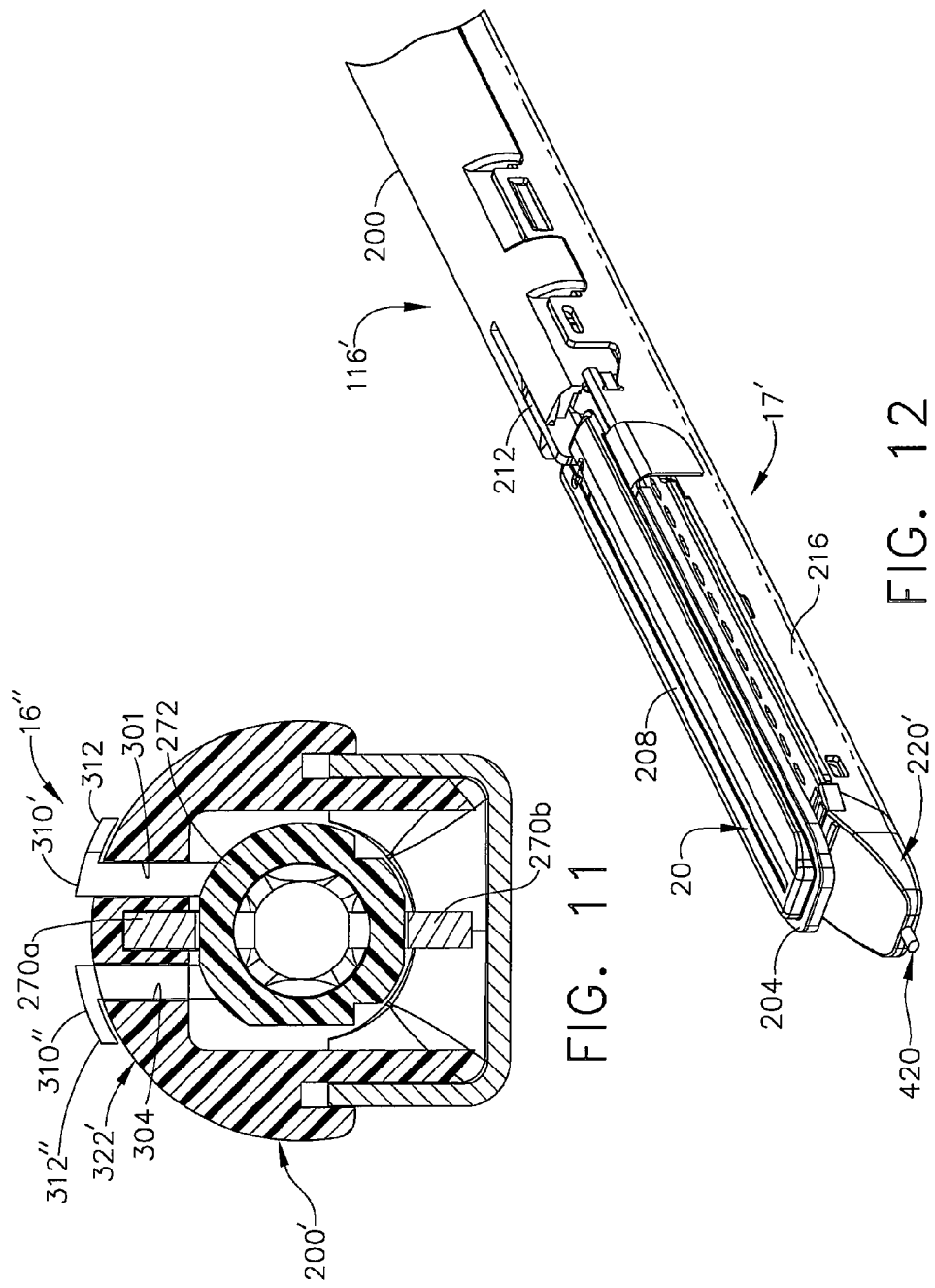

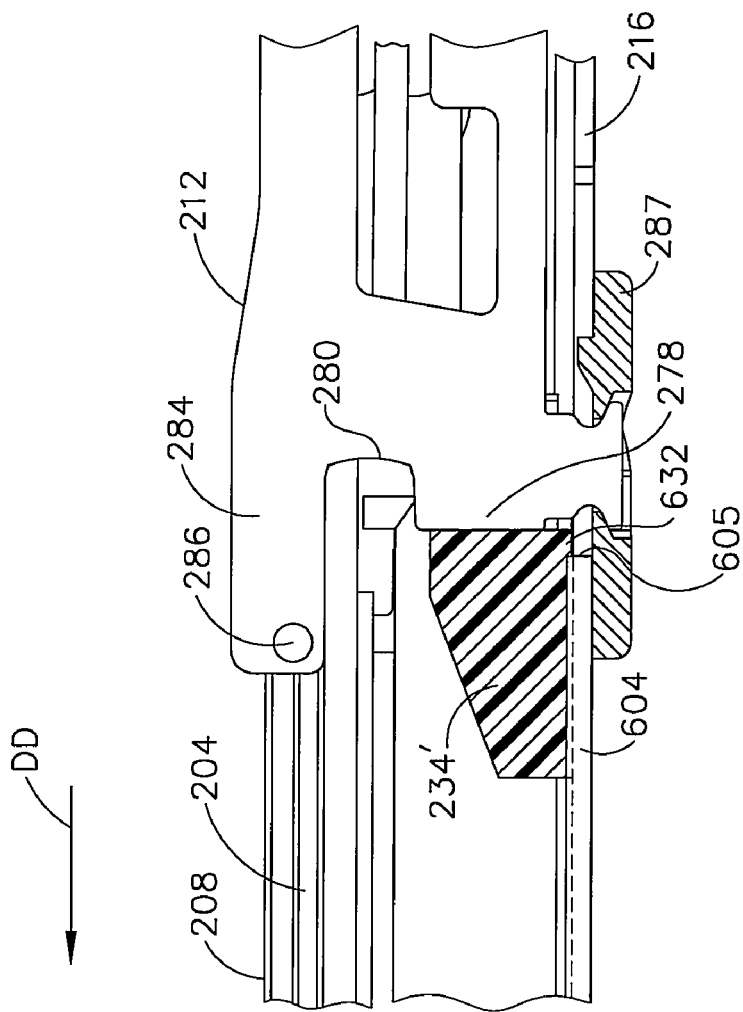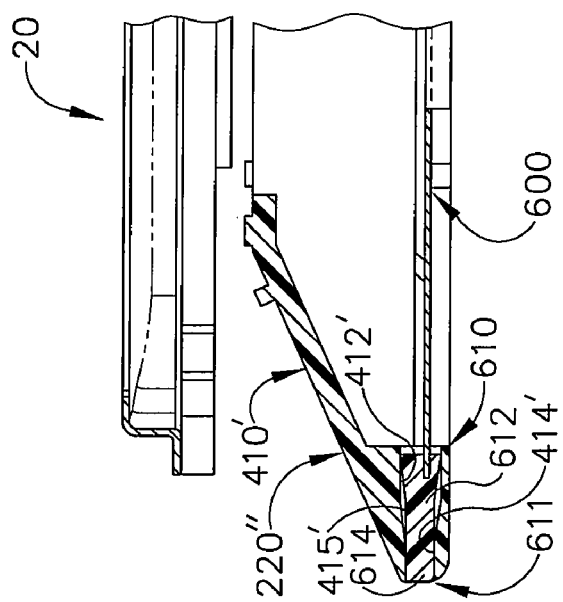
FIG. 21

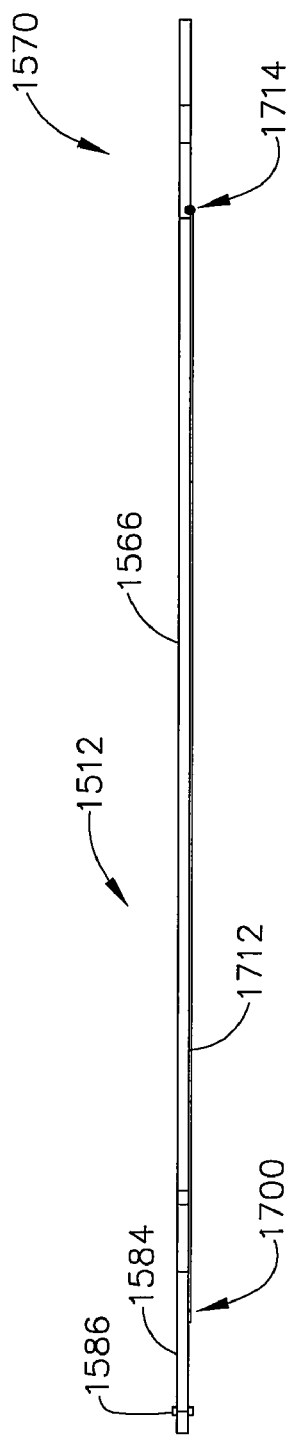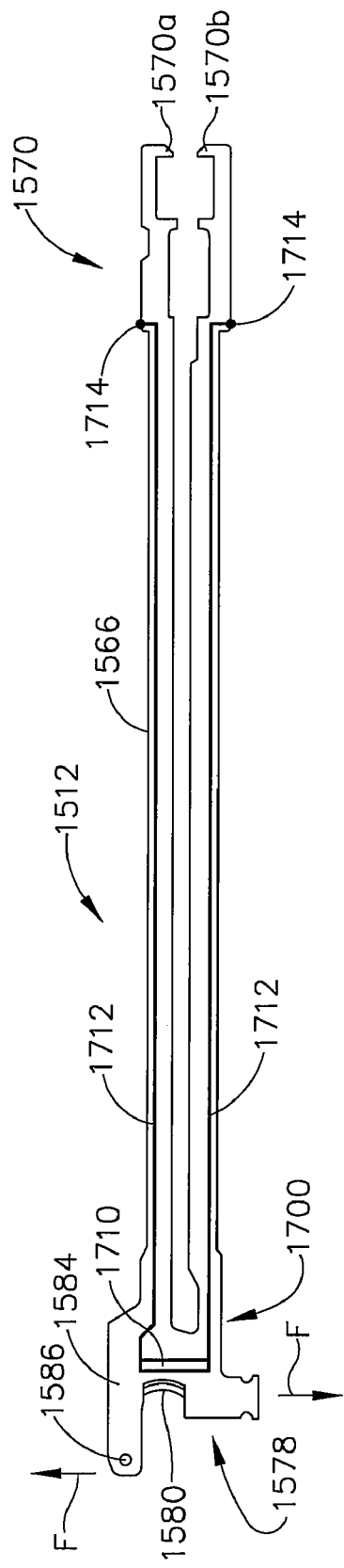

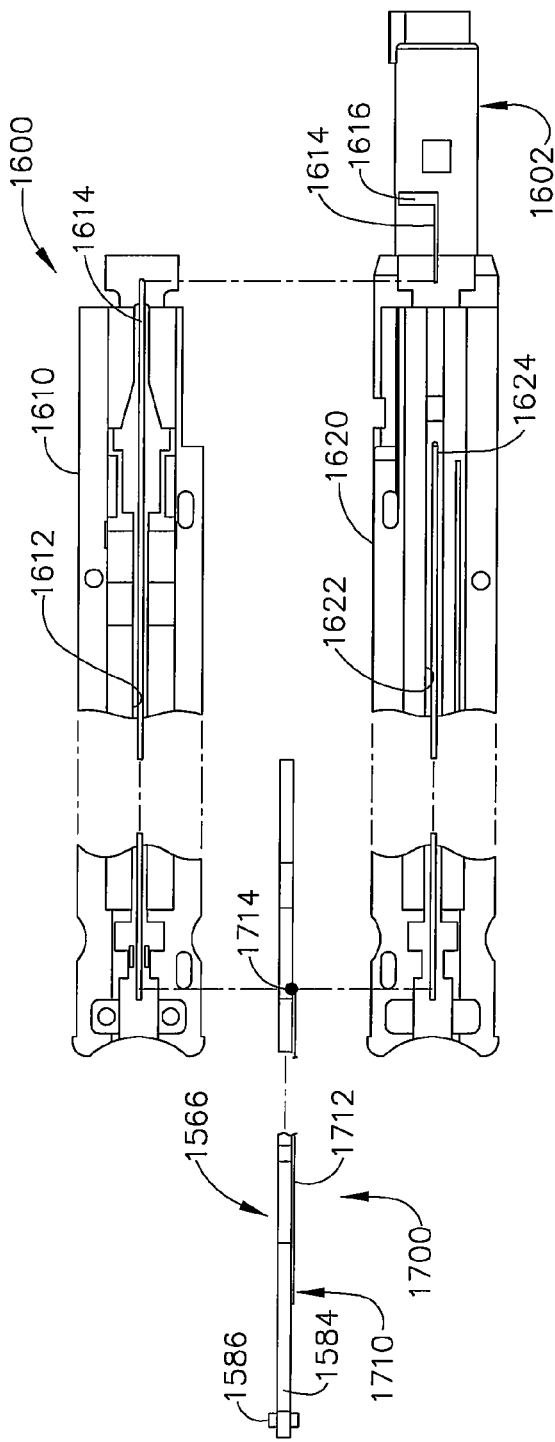
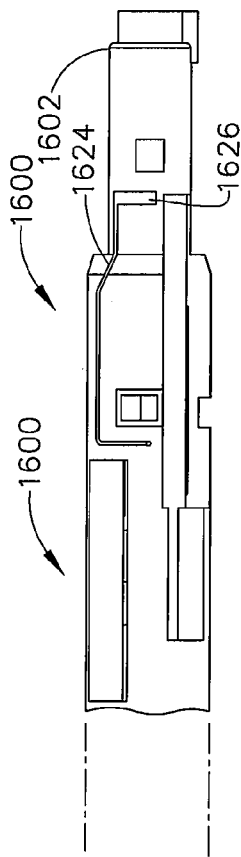
FIG. 33
FIG. 34

DISPOSABLE LOADING UNIT WITH FIRING INDICATOR

COMMONLY OWNED PATENT APPLICATION

U.S. patent application Ser. No. 12/031,624, now U.S. Patent Publication No. 2009/0206144 A1 entitled Disposable Loading Unit With User Feedback Features and Surgical Instrument For Use Therewith to Kevin Doll et al., filed Feb. 14, 2008, the disclosure of which is herein incorporated by reference.

FIELD OF THE INVENTION

The present invention relates in general to endoscopic surgical instruments including, but not limited to, surgical stapler instruments that have disposable loading units that are capable of applying lines of staples to tissue while cutting the tissue between those staple lines and, more particularly, to improvements relating to such disposable loading units.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members supports a staple cartridge that has at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

One type of surgical stapling instrument is configured to operate with disposable loading units (DLU's) that are constructed to support a staple cartridge and knife assembly therein. Once the procedure is completed, the entire DLU is discarded. Such instruments that are designed to accommodate DLU's purport to offer the advantage of a "fresh" knife blade for each firing of the instrument. Examples of such surgical stapling apparatuses and DLU's are disclosed in U.S. Pat. No. 5,865,361 to Milliman et al., the disclosure of which is herein incorporated by reference in its entirety.

Some prior disposable loading units have a slot in the bottom of the carrier channel that supports the staple cartridge. A portion of the drive beam that supports the blade extends out through the slot and a support foot or member is attached thereto. Numbered lines are printed on the bottom of the carrier to enable the clinician to ascertain the progress of the blade as it is driven through the staple cartridge. While such arrangement enables the clinician to monitor the firing progress, it requires the clinician to always be able to view the bottom of the carrier channel during the operation. However, because such units are capable of rotating, often times the unit may be oriented in such a way as to prevent viewing of the bottom of the carrier rendering such system useless.

Moreover, prior surgical stapling apparatuses, such as those disclosed in U.S. Pat. No. 5,865,361 and others, lack means that would enable the clinician to quickly ascertain whether the disposable loading unit was previously used. Such prior surgical stapling apparatuses also lack means for determining how many times a handle assembly was used. Those prior apparatuses also lack means for monitoring the amount of firing force that is being generated during the firing process.

Thus, there is a need for a surgical stapling apparatus configured for use with a disposable loading unit and also has means for monitoring the firing progress of the disposable loading unit, regardless of the position of the unit.

There is also a need for a disposable loading unit that is equipped with means for determining whether a disposable loading unit has ever been fired.

There is still another need for a surgical stapling apparatus that employs a disposable loading unit that has means for indicating the number of times that the surgical stapling apparatus has been fired.

Another need exists for a surgical stapling apparatus that has means for indicating the amount of stress experienced by the blade during the firing of the instrument.

SUMMARY

In one general aspect of various embodiments of the present invention, there is provided a disposable loading unit for attachment to a surgical stapling apparatus. In various embodiments, the disposable loading unit may comprise a staple cartridge that is supported in a carrier that is operably couplable to the surgical stapling apparatus. A housing may be coupled to the carrier and be configured for operable attachment to the surgical stapling apparatus. An anvil assembly may be movably coupled to the carrier for selective movable travel between open and closed positions relative to the staple cartridge. The disposable loading unit may further comprise an axial drive assembly that is constructed to move in a distal direction from a start position to an end position through the staple cartridge in response to a drive motion imparted to the axial drive assembly from the surgical stapling apparatus. A firing indicator assembly may be provided on at least one of the anvil assembly and the housing. The firing indicator assembly may cooperate with the axial drive assembly for indicating a position of the axial drive assembly as the axial drive assembly is driven from the start position to the end position.

In still another general aspect of various embodiments of the present invention, there is provided a disposable loading unit for attachment to a surgical stapling apparatus. In various embodiments, the disposable loading unit includes a staple cartridge that is supported in a carrier that is operably couplable to the surgical stapling apparatus. An anvil assembly may be movably coupled to the carrier for selective movable travel between open and closed positions relative to the staple cartridge. The disposable loading unit may further comprise an axial drive assembly that has a distal end portion that is constructed to move in a distal direction from a start position to an end position through the staple cartridge in response to a drive motion imparted to the axial drive assembly from the surgical stapling apparatus. At least one opening is provided in the anvil assembly such that a portion of the axial drive assembly may be observed as the axial drive assembly is driven from the start position to the end position.

In another general aspect of various embodiments of the present invention, there is provided a disposable loading unit for attachment to a surgical stapling apparatus. In various embodiments, the disposable loading unit comprises a staple cartridge that is supported in a carrier that is operably couplable to the surgical stapling apparatus. An anvil assembly may be movably coupled to the carrier for selective movable travel between open and closed positions relative to the staple cartridge. The disposable loading unit may further comprise an axial drive assembly that has a distal end portion that is constructed to move in a distal direction from a start position to an end position through the staple cartridge in response to a drive motion imparted to the axial drive assembly from the surgical stapling apparatus. A firing indicator may be movably supported on the anvil assembly for contact by a portion of the axial drive assembly as the axial drive assembly is driven from the start position to the end position.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of various embodiments of the invention given above, and the detailed description of the embodiments given below, serve to explain various principles of the present invention.

FIG. 2 is an enlarged perspective view of a portion of the disposable loading unit embodiment of FIG. 1.

FIG. 3 is a cross-sectional view of the disposable loading unit embodiment of FIGS. 1 and 2 taken along line 3-3 in FIG. 1.

FIG. 11 is a cross-sectional view of another disposable loading unit embodiment of the present invention.

FIG. 12 is a perspective view of another disposable loading unit of the present invention with the spent cartridge indicator pin extended.

FIG. 21 is a side cross-sectional view of a portion of a disposable loading unit embodiment of the present invention with some components shown in full view for clarity and with the anvil in a closed position.

FIG. 31 is a top view of an axial drive assembly embodiment of the surgical stapling apparatus depicted in FIG. 30.

FIG. 32 is a side view of the axial drive assembly of FIG. 31.

FIG. 33 is an exploded assembly view of a portion of the axial drive assembly and a portion of a housing of a disposable loading unit embodiment of the present invention.

FIG. 34 is a side elevational view of the portion of the housing depicted in FIG. 33.

DETAILED DESCRIPTION

Figure 1:
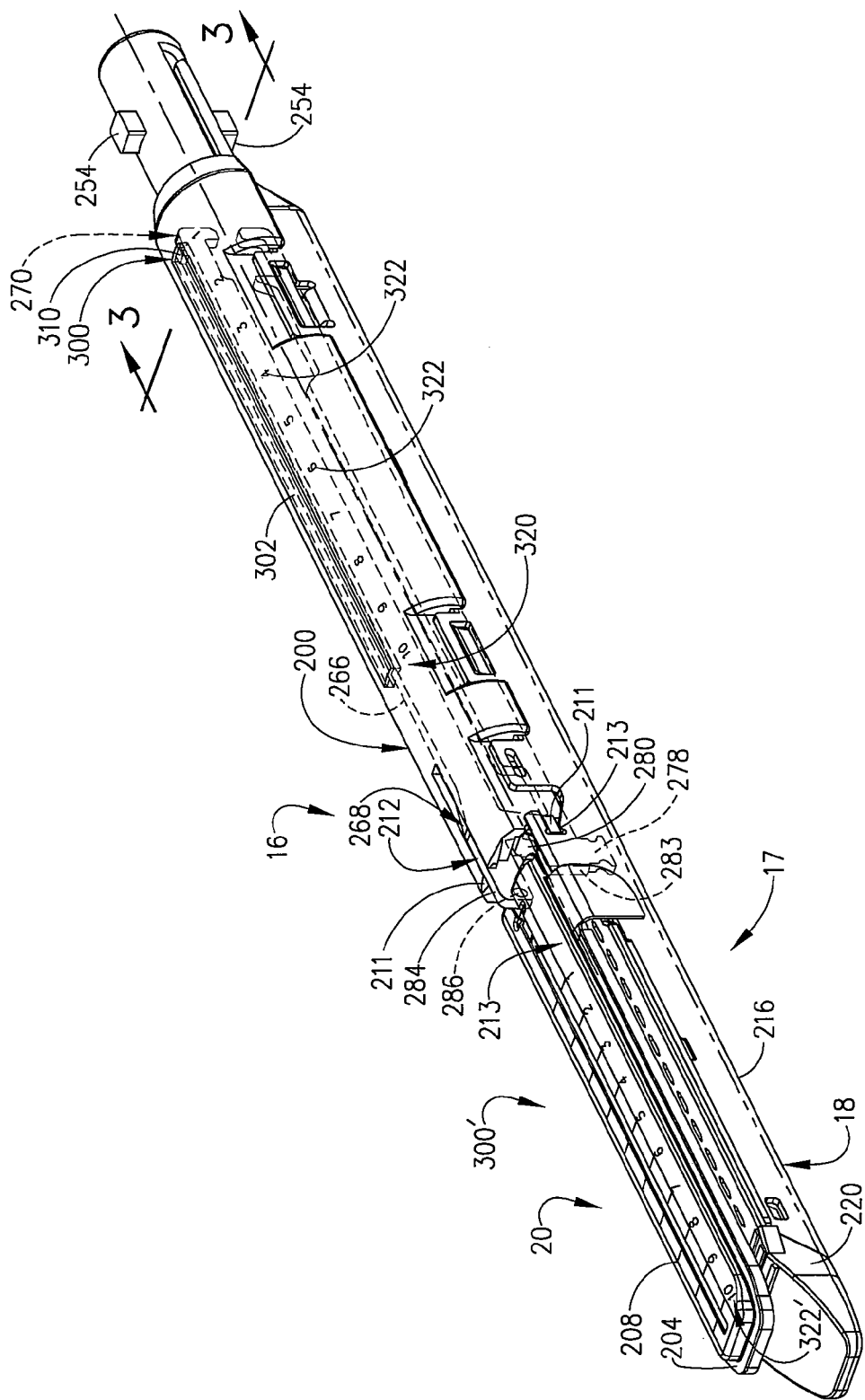
FIG. 1 is a perspective view of a disposable loading unit embodiment of the present invention.
Figure 3A:
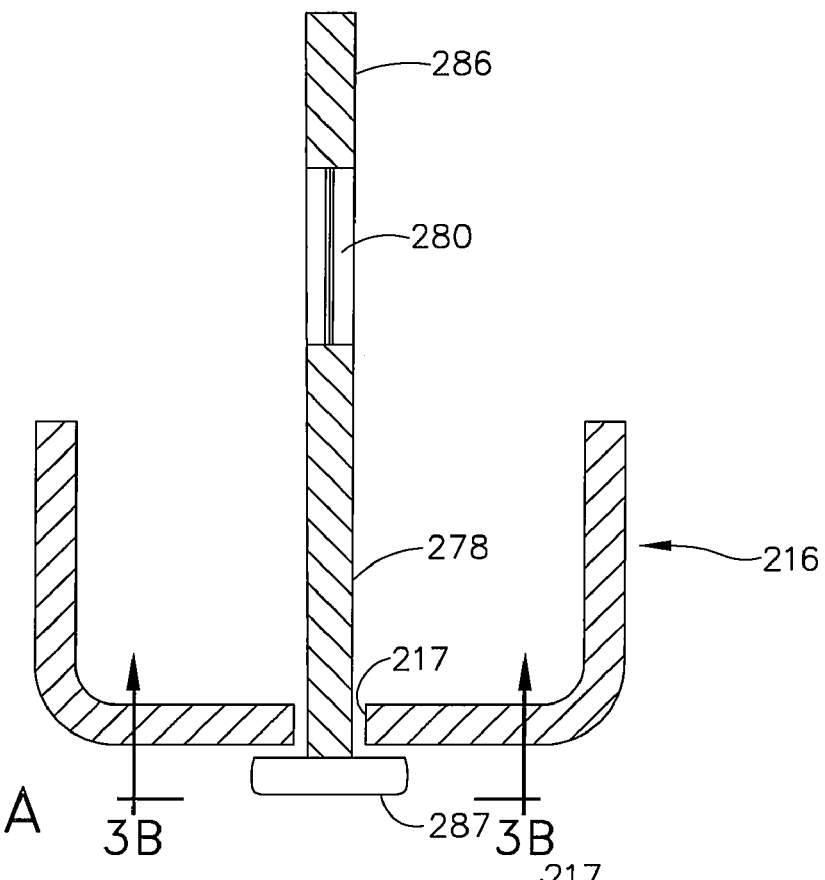
FIG. 3A is a cross-sectional view of a portion of a carrier and an axial drive assembly.
Figure 3B:
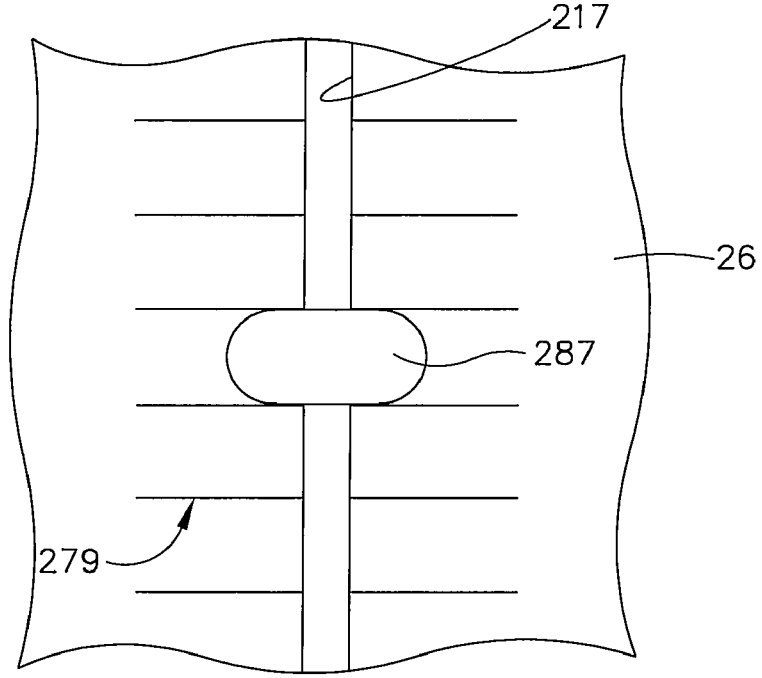
FIG. 3B is a partial bottom view of the carrier and axial drive assembly of FIG. 3A.
Figure 4:
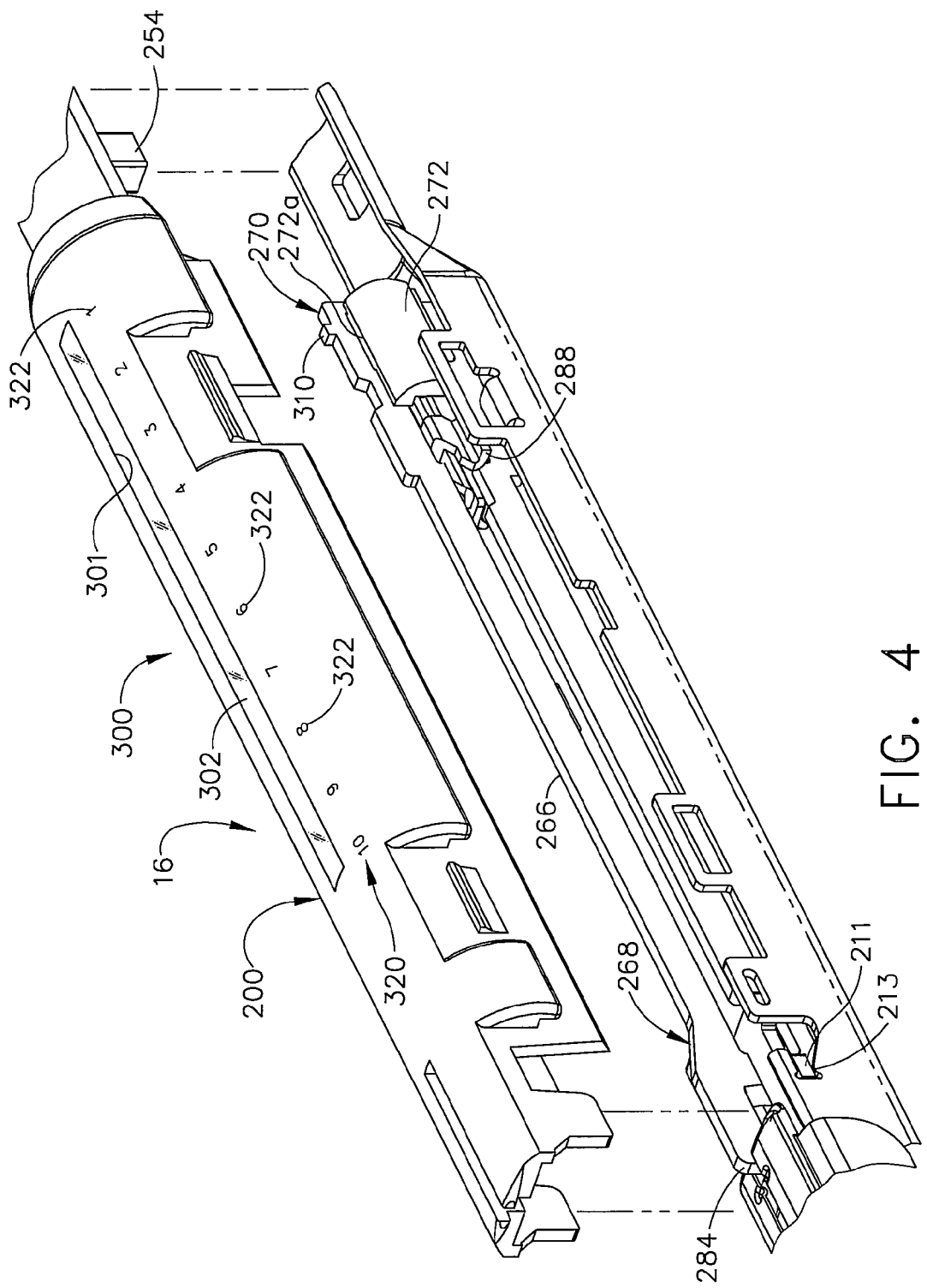
FIG. 4 is an exploded assembly view of a portion of the disposable loading unit of FIGS. 1-3.

Turning to the Drawings, wherein like numerals denote like components throughout the several views, FIG. 1 depicts a disposable loading unit 16 of the present invention that may be used in connection with a surgical stapling apparatus such as those disclosed in U.S. Pat. No. 5,865,361, the disclosure of which has been herein incorporated by reference. It will be appreciated that the terms "proximal" and "distal" are used herein with reference to a clinician gripping a handle assembly of the surgical stapling apparatus to which the disposable loading unit 16 is attached. Thus, the disposable loading unit 16 is distal with respect to the more proximal handle assembly. It will be further appreciated that, for convenience and clarity, spatial terms such as "vertical", "horizontal", "up", "down", "right", and "left" are used herein with respect to the drawings. However, surgical instruments are used in many orientations and positions, and these terms are not intended to be limiting and absolute.

As can be seen in FIG. 1, the disposable loading unit 16 may generally comprise a tool assembly 17 for performing surgical procedures such as cutting tissue and applying staples on each side of the cut. The tool assembly 17 may include a cartridge assembly 18 that houses a plurality of surgical staples therein. The tool assembly 17 may also include a staple-forming anvil assembly 20 that has an anvil portion 204 that has a plurality of staple deforming concavities (not shown) formed in the undersurface thereof. A cover plate 208 may be secured to a top surface of anvil portion 204 to define an anvil cavity therebetween. The anvil cavity is dimensioned to receive a distal end of an axial drive assembly 212. The axial drive assembly 212 may comprise a drive beam 266 of the type and construction described in U.S. Pat. No. 5,865,361. A longitudinal slot (not shown) may extend through anvil portion 204 to facilitate passage of retention flange 284 of axial drive assembly 212 into the anvil cavity. A pair of pivot members 211 may be formed on the proximal end of the anvil portion 204 and be configured to be received in slots 213 that are formed in carrier 216 to enable the anvil portion 204 to pivot between the open and tissue-clamping positions. A camming surface (not shown) may be formed on a proximal end of anvil portion 204 and is positioned to engage axial drive assembly 212 to facilitate closing of the anvil assembly 20.

The distal end of drive beam 266 may include a vertical support strut 278 which supports the knife blade 280, and an abutment surface 283 which engages the central portion of actuation sled 234 during a stapling procedure. Knife blade 280 may be generally positioned to translate slightly behind actuation sled 234 through a central longitudinal slot in staple cartridge 220 to form an incision between rows of stapled body tissue. A retention flange 284 may project distally from vertical strut 278 and support a camming pin 286 at its distal end. Camming pin 286 may be dimensioned and configured to engage camming surface on anvil portion 204 to clamp anvil portion 204 against body tissue. In addition, a leaf spring (not shown) may be provided between the proximal end of the anvil portion 204 and the distal end portion of the housing 200 to bias the anvil assembly 20 to a normally open position. The disposable loading unit 16 may further include a lockout device 288 as described in U.S. Pat. No. 5,865,361.

The disposable loading unit 16 may further include a cartridge assembly 18. The cartridge assembly 18 may generally include a carrier 216 which is dimensioned and configured to receive a staple cartridge 220 therein. Such staple cartridge 220 supports a plurality of fasteners (staples) and pushers as is known in the art. The staple cartridge 220 may be configured as described in U.S. Pat. No. 5,865,361 to accommodate upstanding cam wedges of an actuation sled. A central longitudinal slot may extend along the length of staple cartridge 220 to facilitate passage of a knife blade 280 formed on the axial drive assembly 212. During operation of the disposable loading unit 16, the actuation sled translates through longitudinal slots of staple cartridge 220 to advance cam wedges into sequential contact with the pushers that are operably supported in the staple cartridge 220 to cause the pushers to translate vertically within the staple cartridge 220 and urge the fasteners (staples) associated with the pushers into the staple deforming cavities of the anvil assembly 20. The carrier 216 may also have an elongated bottom slot therethrough through which a portion of the vertical support strut may extend to enable the clinician to view the firing progress of the distal end of the drive beam as is described and shown in U.S. Patent No. 5,865,361. In addition, firing indicia (numbers, lines, etc.) may be printed or otherwise provided on the bottom of the carrier 216 adjacent the bottom slot for indicating the position of the distal end of the drive beam during the firing sequence as is known in the art.

As can also be seen in FIG. 1, the disposable loading unit 16 may also have a housing portion 200 that is adapted to snap onto or otherwise be attached to the carrier 216. The axial drive assembly 212 may include an elongated drive beam 266 that has a distal working head 268 and a proximal engagement section 270. The proximal end of housing 200 may include engagement nubs 254 for releasably engaging elongated body of a surgical stapling apparatus. Nubs 254 form a bayonet type coupling with the distal end of the elongated body portion of the surgical stapling apparatus as described in U.S. Pat. No. 5,865,361. The drive beam 266 may be constructed from a single sheet of material or, preferably, from multiple stacked sheets. Engagement section 270 may include a pair of engagement fingers 270a and 270b that are dimensioned and configured to mountingly engage a pair of corresponding retention slots 272a formed in a drive connector 272. Drive connector 272 may include a proximal porthole (not shown) that is configured to receive the distal end of a control rod as discussed in U.S. Pat. No. 5,865,361. The control rod may impart a driving motion and a retraction motion to the axial drive assembly 212 in a known manner to drive the axial drive assembly 212 from a start position wherein the knife blade has not been advanced through any tissue and an end position wherein the distal end of the axial drive assembly 212 has advanced through the staple cartridge 220 to fire all of the staples therein and sever the tissue clamped between the cartridge 220 and the anvil 20 and then back to the start position.

As can be most particularly seen in FIGS. 1-4, the disposable loading unit 16 may also include a firing indicator assembly 300. As was discussed above, prior units employed a slot in the bottom of the carrier to enable the clinician to ascertain the progress of the blade as it is driven through the staple cartridge. While such arrangement enables the clinician to monitor the firing progress, it requires the clinician to always be able to view the bottom of the carrier channel during the operation. However, because such units are capable of rotating, often times the unit may be oriented in such a way as to prevent viewing of the bottom of the carrier rending such system useless. Various embodiments of the present invention solve that problem. For example, in various embodiments of the present invention, the firing indicator assembly 300 may include an axially extending opening 301 formed along the top dead center of the housing 200. In some embodiments, a transparent window 302 may be mounted (e.g., glued, snapped, etc.) in the opening 301. In other embodiments, no window is provided. In the embodiment depicted in FIGS. 1-4, the engagement section 270 has an indicator 310 formed thereon that is adapted to ride in the opening 301 and is viewable through the window 302. A firing scale 320, which may comprise various forms of indicia 322 (e.g., numbers, letters, colors or combinations of numbers, letters and/or colors), may be provided on the housing 200. The indicia 322 may be located at positions on the housing 200 to enable the clinician to assess the progress of the firing process (i.e., the distance that the axial drive assembly 212 has been advanced axially through the staple cartridge 220) by viewing the position of the indicator 310 relative to the indicia 322.

Those of ordinary skill in the art will appreciate that the firing indicator assembly 300 may be employed on disposable loading units that also have the slot 217 through the bottom of the carrier 216 which enables a portion of the vertical strut 278 to extend therethrough. A support member 287 is attached to the bottom of the vertical strut 278. See FIGS. 3A and 3B. Bottom firing indicia 279 may be provided adjacent the slot 217 to enable the clinician to monitor the advancement of the axial drive assembly also when viewing the bottom of the disposable loading unit. By combining these features with the firing indicator assembly 300 of the present invention, the clinician is able to monitor the firing progress regardless of whether the clinician is able to view the top of the unit or the bottom of the unit.

Other firing indicator arrangements 300' of the present invention comprise an axially extending anvil slot 209 through the anvil cover plate 208 that enables the clinician to view the of retention flange 284 of axial drive assembly 212 as the axial drive assembly is driven from the start position to the end position through the cartridge 220. Although one continuous axial slot 209 is illustrated, in various other embodiments, the slot 209 may comprise a series of slot segments (not shown). Anvil firing indicia 322' may be provided on the anvil cover 208 adjacent the slot 209. In still other embodiments, to enhance the visibility of the retention flange, the retention flange 284 may be provided with a color 211 that differs from a color 213 of the anvil assembly 20.

Figure 5:
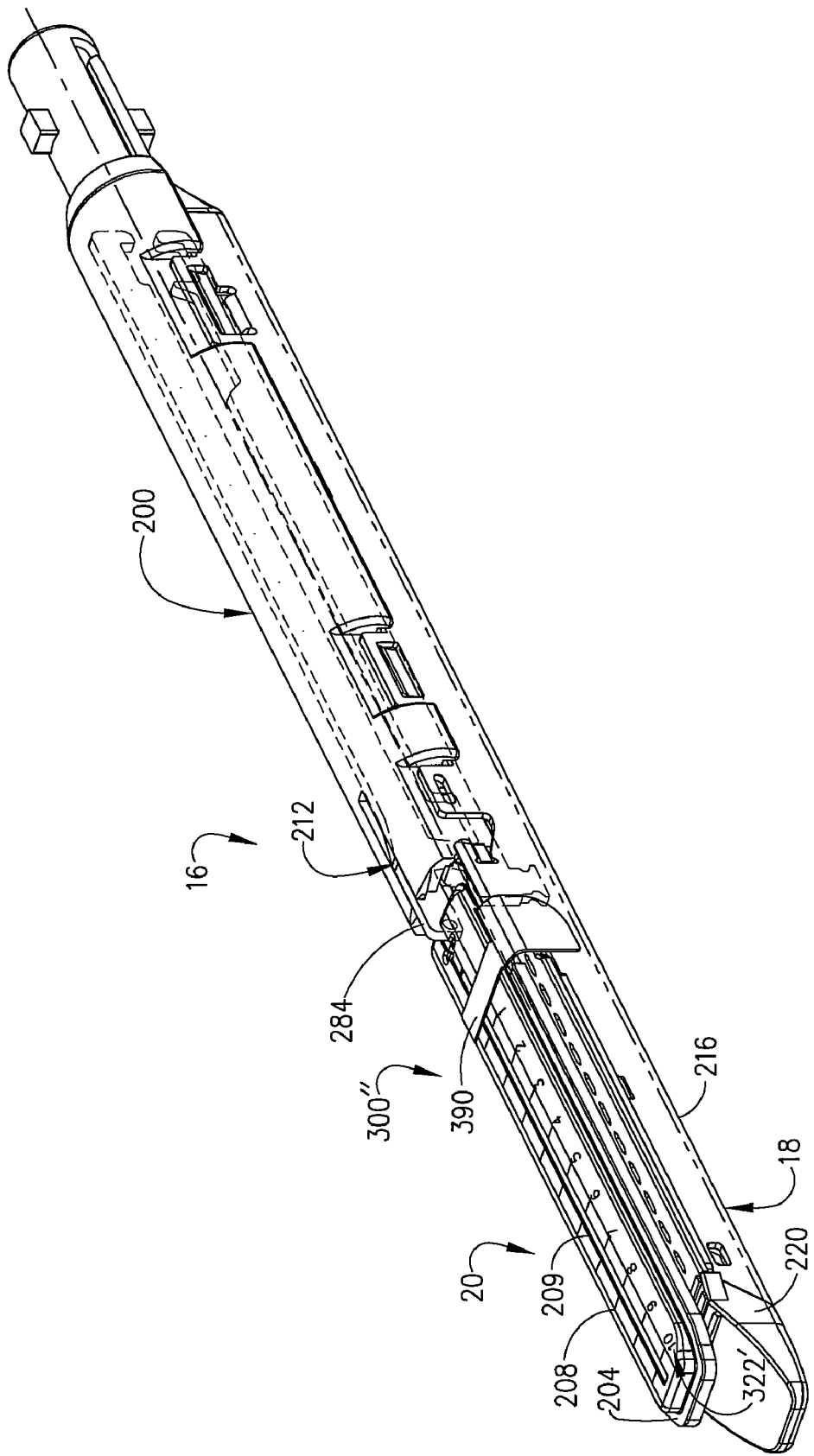
FIG. 5 is a perspective view of another disposable loading unit embodiment of the present invention.
Figure 6:
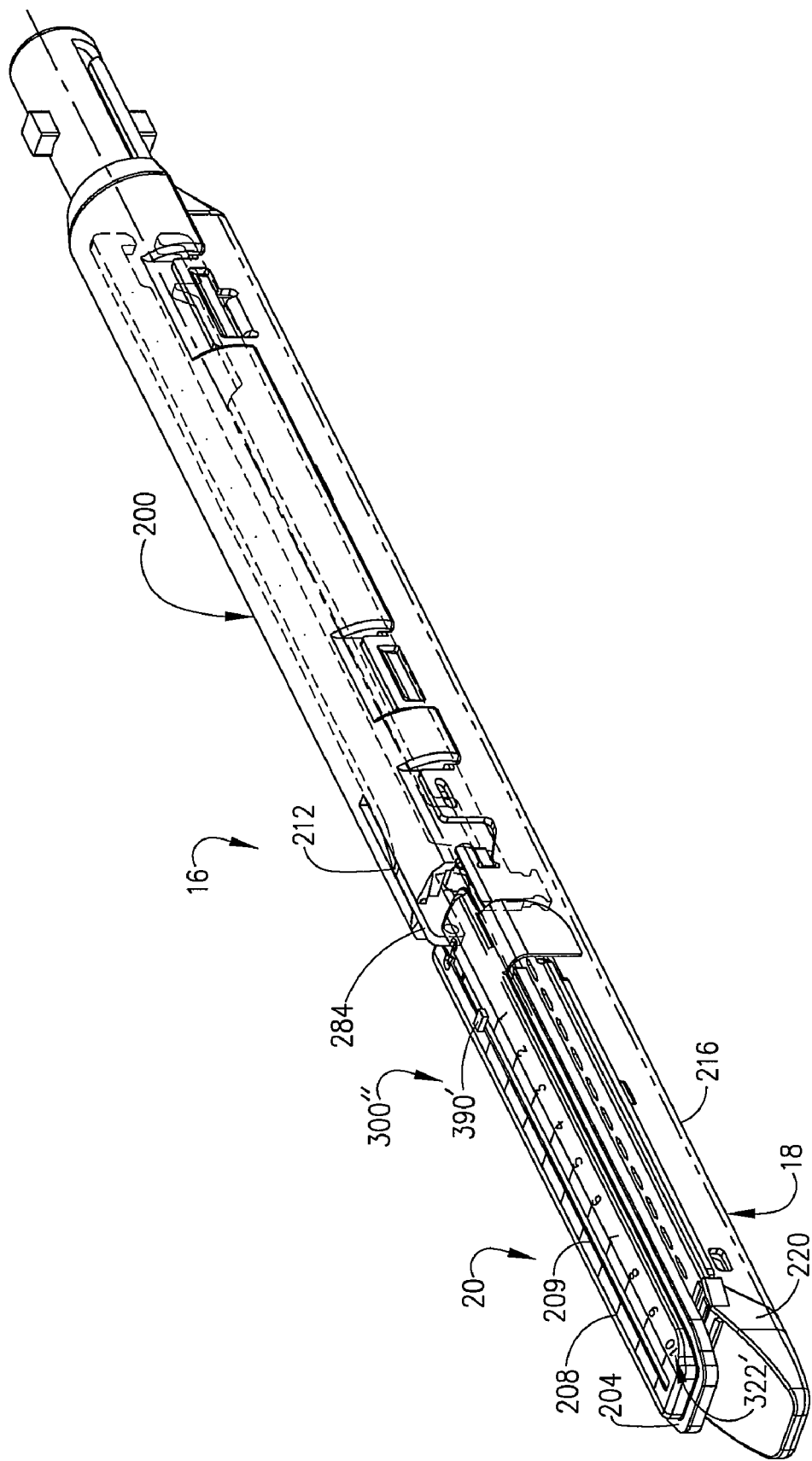
FIG. 6 is a perspective view of another disposable loading unit embodiment of the present invention.

FIG. 5 illustrates yet another firing indicator arrangement 300". As can be seen in that Figure, a movable firing indicator 390 is retained on the anvil cover 208 and is arranged to be contacted by the retention flange 284 as the axial drive assembly 212 is driven from the start position to the end position. Thus, the clinician may monitor the firing progress by viewing the position of the firing indicator 390 on the anvil 20. The person of ordinary skill in the art will understand that such an indicator 390 may also serve to strengthen the anvil cover assembly 208. In alternative embodiments, the indicator 390' may be movably mounted within the slot 209. See FIG. 6.

Although the disposable loading units describe above comprise a non-articulatable loading unit, the person of ordinary skill in the art will understand that the advantages provided by the firing indicator assemblies 300, 300' and/or 300" may be easily employed in connection with known articulatable disposable loading units such as those disclosed in U.S. Pat. No. 5,865,361 and others.

Figure 7:
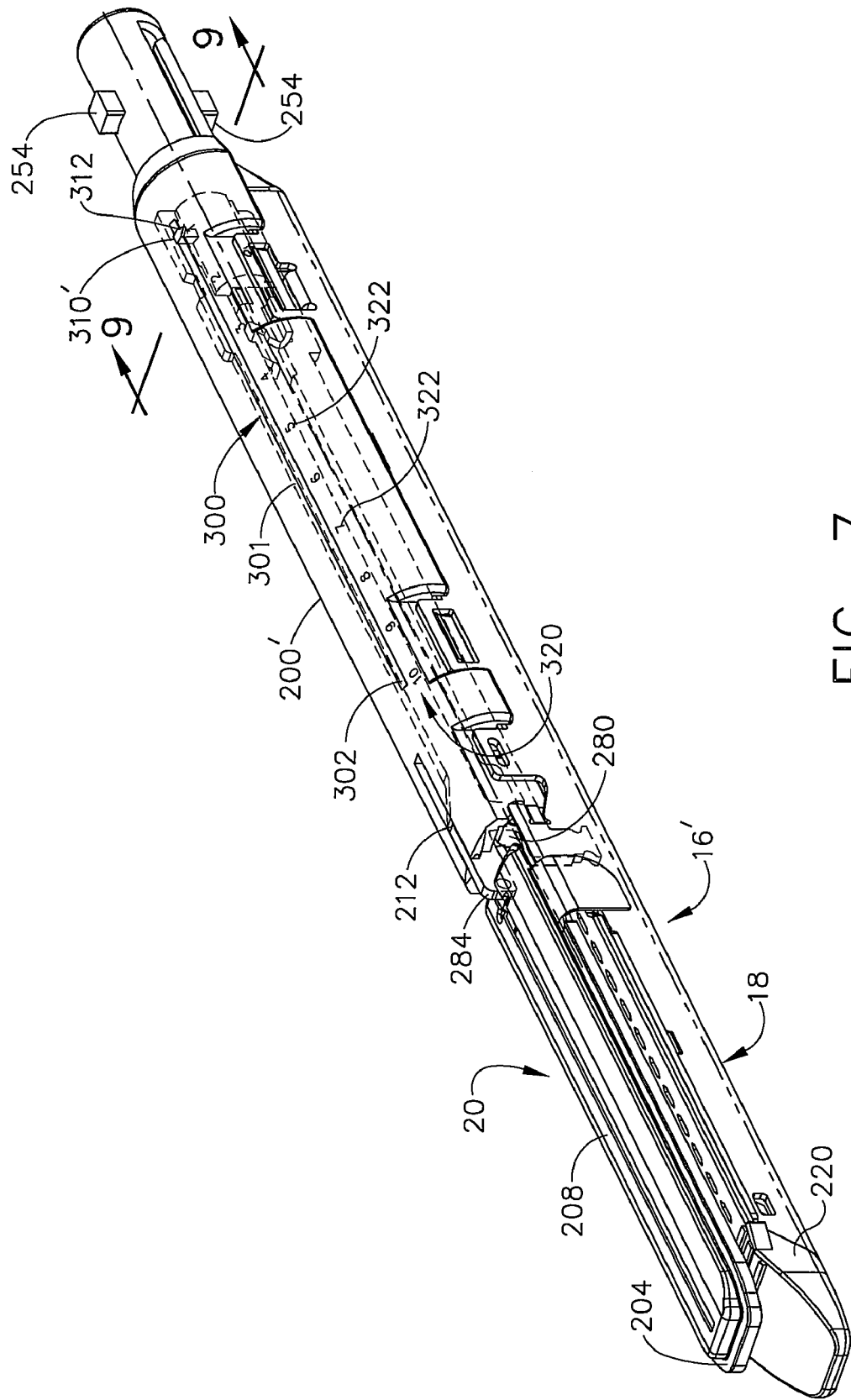
FIG. 7 is a perspective view of another disposable loading unit embodiment of the present invention.
Figures 8, 9:
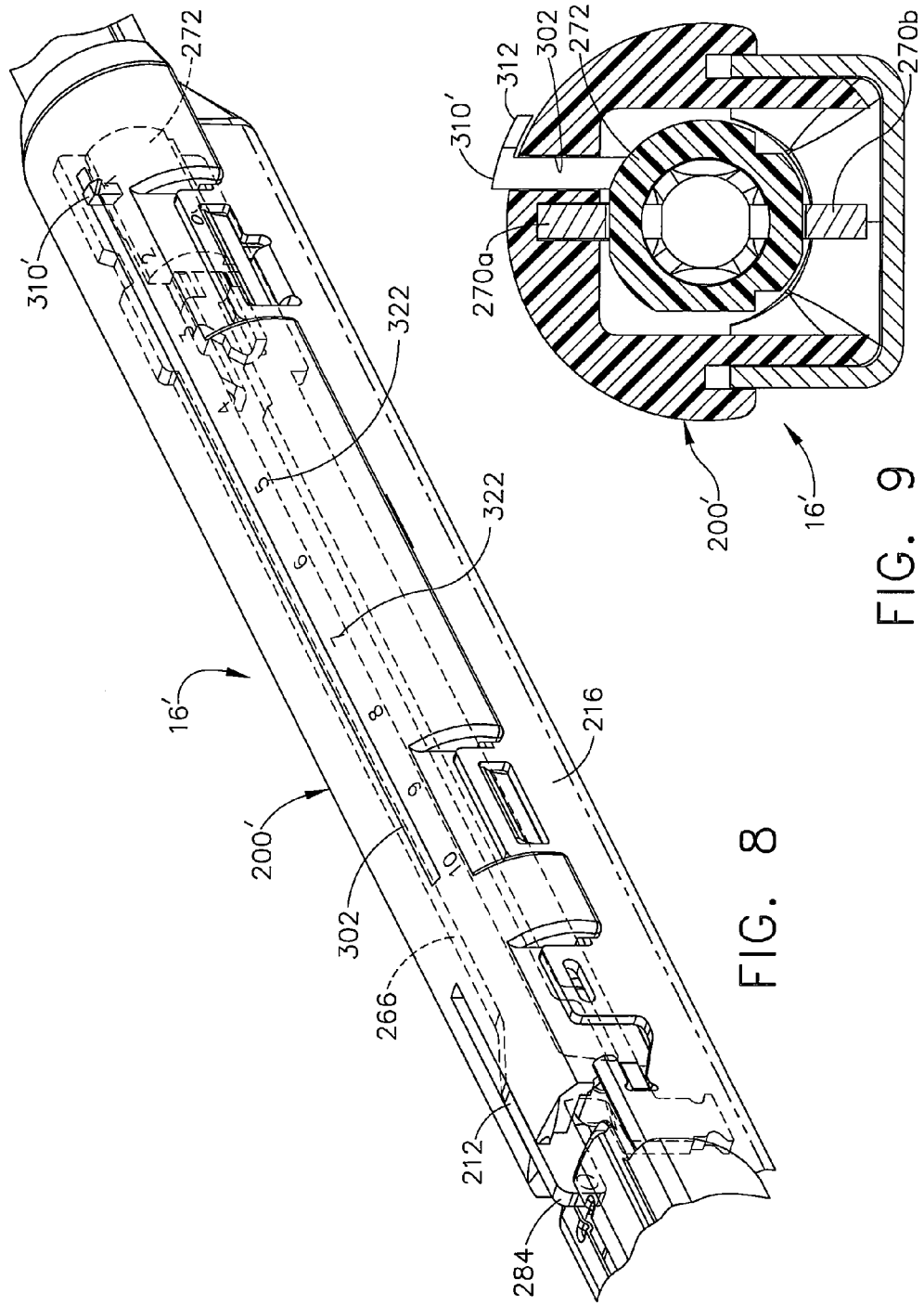
FIG. 8 is an enlarged perspective view of a portion of the disposable loading unit embodiment of FIG. 7.
FIG. 9 is a cross-sectional view of the disposable loading unit embodiment of FIGS. 7 and 8 taken along line 9-9 in FIG. 7.
Figure 10:
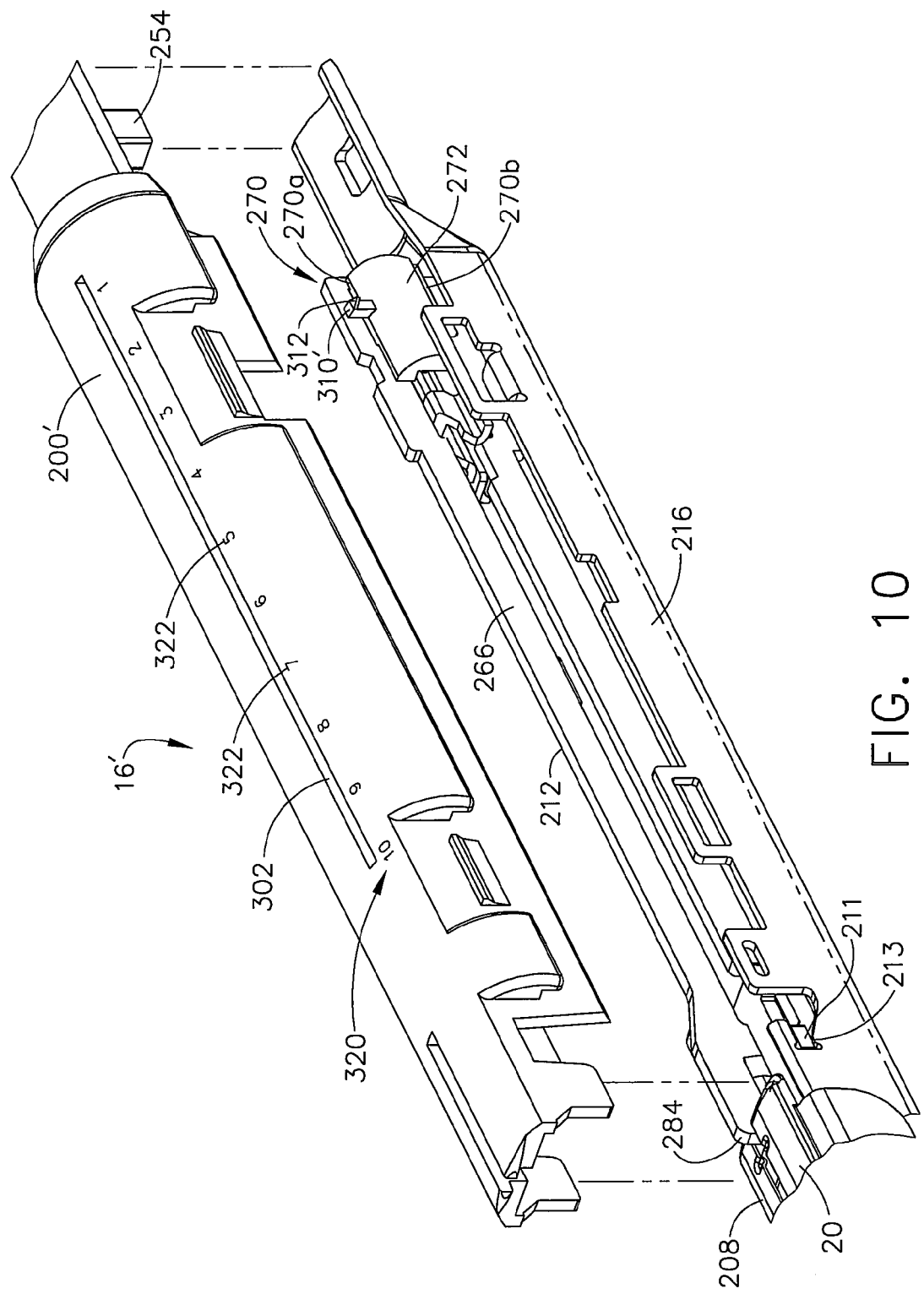
FIG. 10 is an exploded assembly view of a portion of the disposable loading unit embodiment of FIGS. 7-9.

FIGS. 7-9 illustrate another disposable loading unit 16' that may be substantially similar to the disposable loading unit described above, except for the differences noted below. For example, in this embodiment, the firing indicator assembly 300 lacks window 302. In various embodiments, the opening 301 may be located more to one lateral side of the housing 200' and the indicator 310' may actually protrude out through the opening 301 and have a pointer 312 formed thereon to coincide with the indicia 322. Thus, in this embodiment, the indicator 310' runs off of top dead center of the housing 200' to enhance the ability of the clinician to view the indicator 310' from one lateral side of the disposable loading unit 16'. As can be seen in FIG. 9, in various embodiments the indicator 310' protrudes from the drive connector 272. In an alternative disposable loading unit 16" as depicted in FIG. 11, a second opening 304 is provided through housing 200' on the opposing lateral side through which opening 301 extends. A second indicator 310" is attached to the drive connector 272 and protrudes through the opening 304. The second indicator 310" may also have a pointer 312" formed thereon that coincides with indicia 322' provided adjacent the second opening 304 in correspondence with the first indicia 322. Such arrangement permits the clinician to assess the progress of the firing process from either lateral side of the disposable loading unit 16". Again, this embodiment may also be employed in connection with articulatable disposable loading units without departing from the spirit and scope of the present invention.

Figure 13:
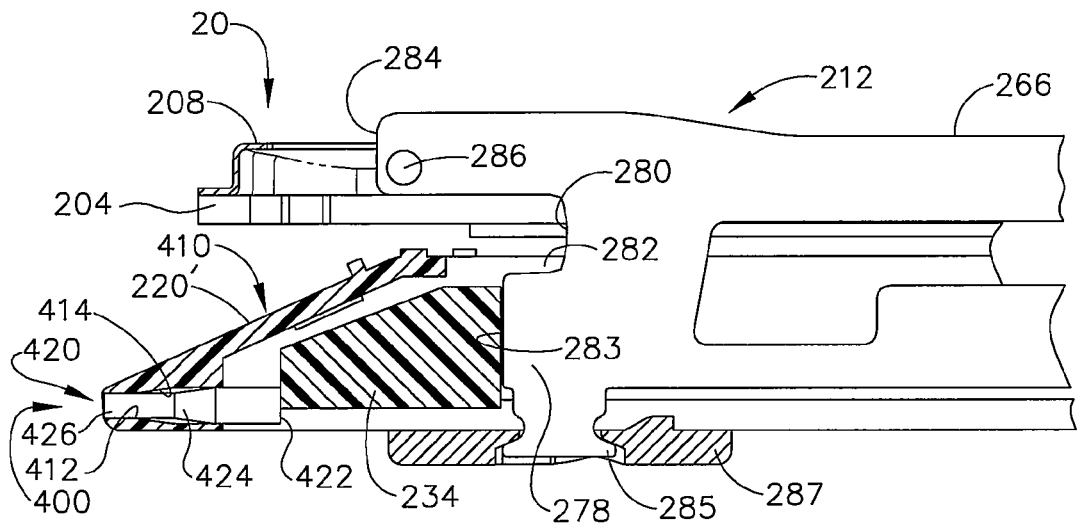
FIG. 13 is a side cross-sectional view of a portion of a disposable loading unit embodiment of the present invention with some components shown in full view for clarity and wherein the spent cartridge indicator pin is completely received within the nose of the staple cartridge.
Figure 14:
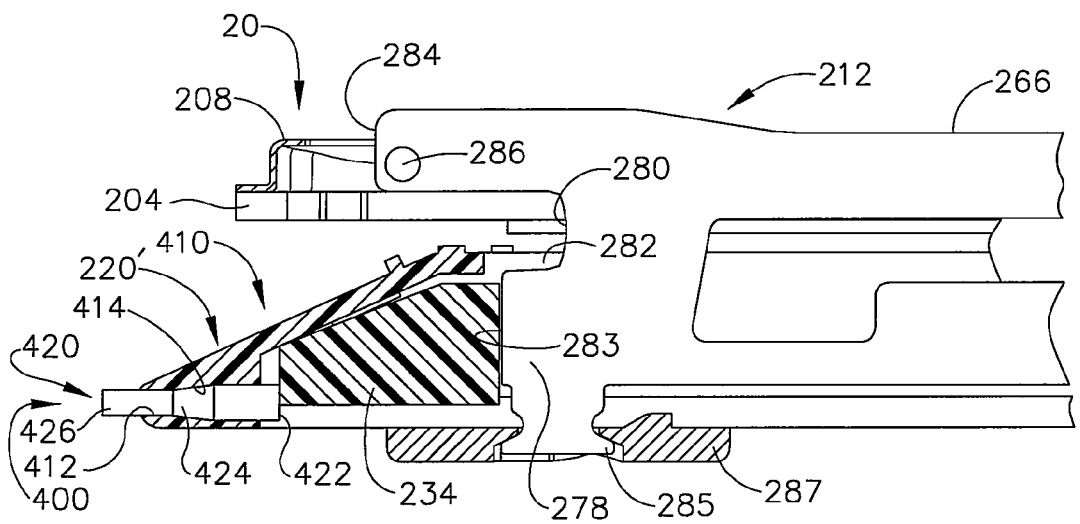
FIG. 14 is another partial side cross-sectional view of the portion of the disposable loading unit of FIG. 13 with the spent cartridge indicator pin extended.
Figure 15:
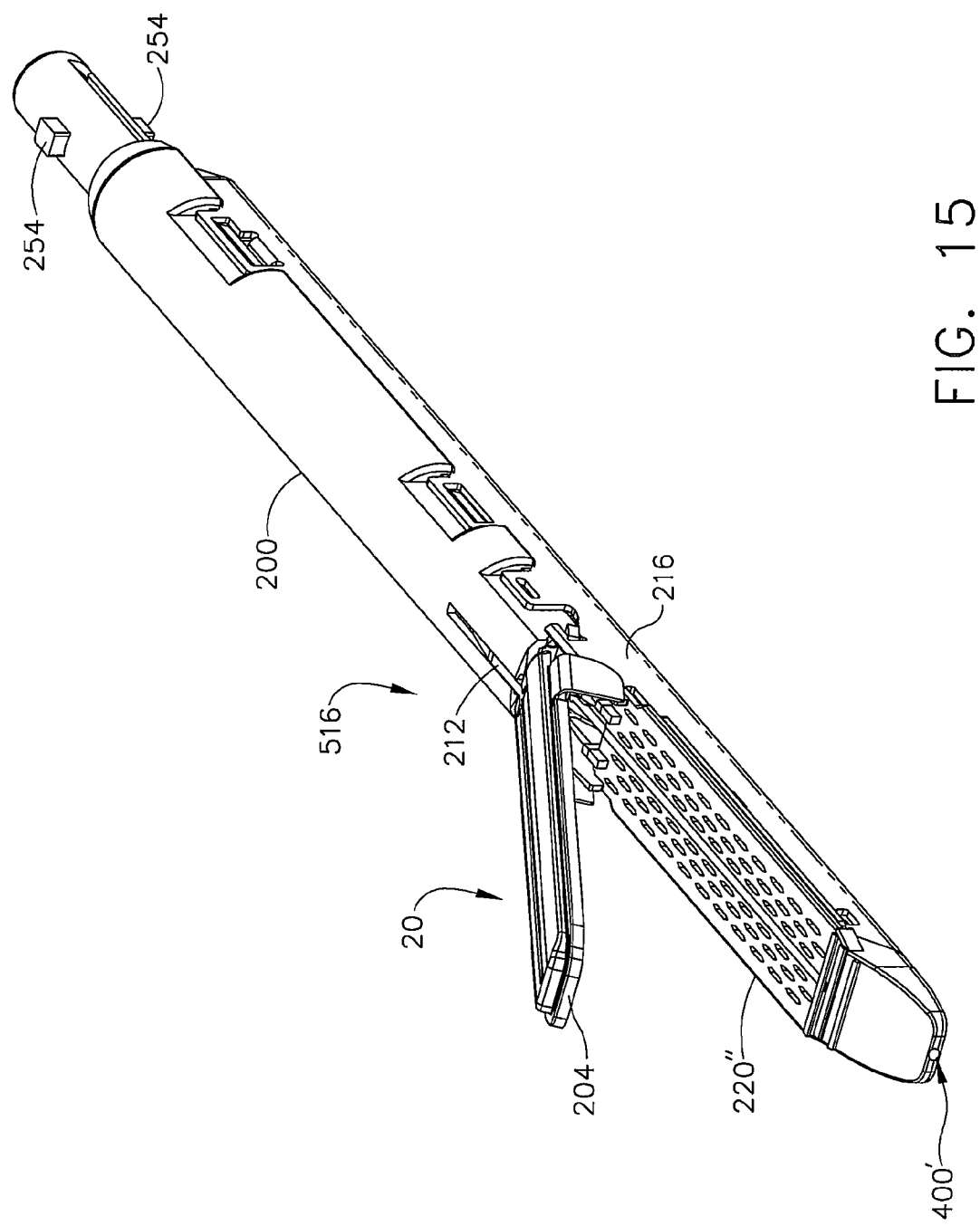
FIG. 15 is a perspective view of another disposable loading unit embodiment of the present invention.

FIGS. 12-14 illustrate another disposable loading unit embodiment 116 of the present invention that may be substantially similar to the disposable loading unit embodiment 16 described above or to those disposable loading units described in U.S. Pat. No. 5,865,361, except for the unique and novel differences noted below. In particular, the disposable loading unit 116 includes a tool assembly 17' that includes a carrier 216 that supports a staple cartridge 220' therein. An anvil assembly 20 may be pivotally attached to the carrier 216 for selective movable travel between open and closed positions relative to the carrier 216 in the manner discussed above. In various embodiments, the tool assembly 17' may include a spent cartridge indication system 400 of the present invention. FIGS. 13 and 14 illustrate a distal portion of the staple cartridge 220' in cross-section. Staple cartridge 220' may comprise a staple cartridge 220 of the type and construction disclosed in U.S. Pat. No. 5,865,361, except for the provision of the spent cartridge indication system 400.

Staple cartridge 220' supports a plurality of fasteners and pushers as is known in the art. A plurality of spaced-apart longitudinal slots may extend through staple cartridge 220' to accommodate upstanding cam wedges of an actuation member or sled 234 that is movably supported within the tool assembly 17' and which is selectively movable from a staring position to an end position therein. A central longitudinal slot 282 extends along the length of staple cartridge 220 to facilitate passage of a knife blade 280 formed on the axial drive assembly 212. During operation of the disposable loading unit 116, actuation sled 234 translates through longitudinal slots of staple cartridge 220' to advance the cam wedges of the actuation sled 234 into sequential contact with the pushers that are operably supported in the cartridge 220' to cause the pushers to translate vertically within the cartridge 220' and urge the fasteners (staples) associated with the pushers into the staple deforming cavities of the anvil assembly 20. The distal end of drive beam 266 includes a vertical support strut 278 which supports the knife blade 280, and an abutment surface 283 which engages the central portion of actuation sled 234 to impart a driving motion thereto during a stapling procedure. Surface 285 is located at the base of surface 283 and is configured to receive a support member 287 that is slidably positioned along the bottom of the carrier 216. Knife blade 280 is generally positioned to translate slightly behind actuation sled 234 through a central longitudinal slot 282 in staple cartridge 220 to form an incision between rows of stapled body tissue.

As can be seen in FIGS. 13 and 14, the spent cartridge indication system 400 may comprise a spent cartridge indicator pin 420 that is supported within the distal end 410 of the staple cartridge 220'. The indicator pin 420 may have a proximal abutment end 422 for abutting contact by the actuation sled 234, a tapered central portion 424, and an indicator portion 426. The indicator pin 420 is received in a hole 412 in the distal end 410 that has a tapered hole segment 414. FIG. 13 illustrates the position of the actuation sled 234 before it has reached the end position and the indicator pin is in an "unfired" position. When the staple cartridge 220' has not yet been fired, the indicator portion 426 of the indicator pin 420 may be completely received within the nose portion 410 of the staple cartridge 220'. As the actuation sled 234 reaches the end position, the actuation sled 234 pushes on the abutment end 422 of the indicator pin 420 causing the tapered portion 424 thereof to lockably engage the internal tapered portion 414 of the hole 412. Thus, the indicator portion 426 of the indicator pin 420 will be pushed out of the distal end 410 of the staple cartridge 220' to a "fired" position and is retained in that position to indicate to the clinician that the staple cartridge 220' has been spent or previously fired. See FIG. 14. Such arrangement enables the clinician to quickly determine whether the disposable loading unit 116 has been previously fired. Those of ordinary skill in the art will appreciate that the unique and novel spent cartridge indication system may be effectively employed in connection with articulatable and non-articulatable disposable loading units alike.

FIGS. 15-25 illustrate another disposable loading unit 516 of the present invention that may be substantially similar to the disposable loading unit 16 described above or to those disposable loading units described in U.S. Pat. No. 5,865,361, except for the unique and novel differences noted below. In particular, the disposable loading unit 516 includes a tool assembly 17 that comprises a carrier 216 that supports a staple cartridge 220" therein. An anvil assembly 20 is pivotally supported relative to the carrier 216 and is selectively movable between open and closed positions relative thereto. The tool assembly 17 may further comprise a spent cartridge indication system 400'. Staple cartridge 220" may comprise a conventional staple cartridge of the type and construction disclosed in U.S. Pat. No. 5,865,361, except for the differences noted below.

As indicated above, staple cartridge 220" supports a plurality of fasteners (staples) and pushers as is known in the art. A plurality of spaced-apart longitudinal slots 235 (FIG. 20) extend through staple cartridge 220" to accommodate upstanding cam wedges 232 of an actuation member or sled 234'. See FIG. 18. A central longitudinal slot 282 extends along the length of staple cartridge 220" to facilitate passage of a knife blade 280 formed on the axial drive assembly 212. See FIG. 20. During operation of the disposable loading unit 516, actuation sled 234' translates through longitudinal slots 235 of staple cartridge 220" to advance the cam wedges 232 of the actuation sled 234' into sequential contact with the pushers that are operably supported in the cartridge 220" to cause the pushers to translate vertically within the cartridge 220" and urge the fasteners (staples) associated with the pushers into the staple deforming cavities of the anvil assembly 20. The distal end of drive beam 266 includes a vertical support strut 278 which supports the knife blade 280, and an abutment surface 283 which engages the central portion of actuation sled 234 during a stapling procedure. See FIG. 19. Surface 285 is located at the base of surface 283 and is configured to receive a support member 287 that is slidably positioned along the bottom of the carrier 216. Knife blade 280 is generally positioned to translate slightly behind actuation sled 234' through a central longitudinal slot 282 in staple cartridge 220 to form an incision between rows of stapled body tissue.

Figure 16:
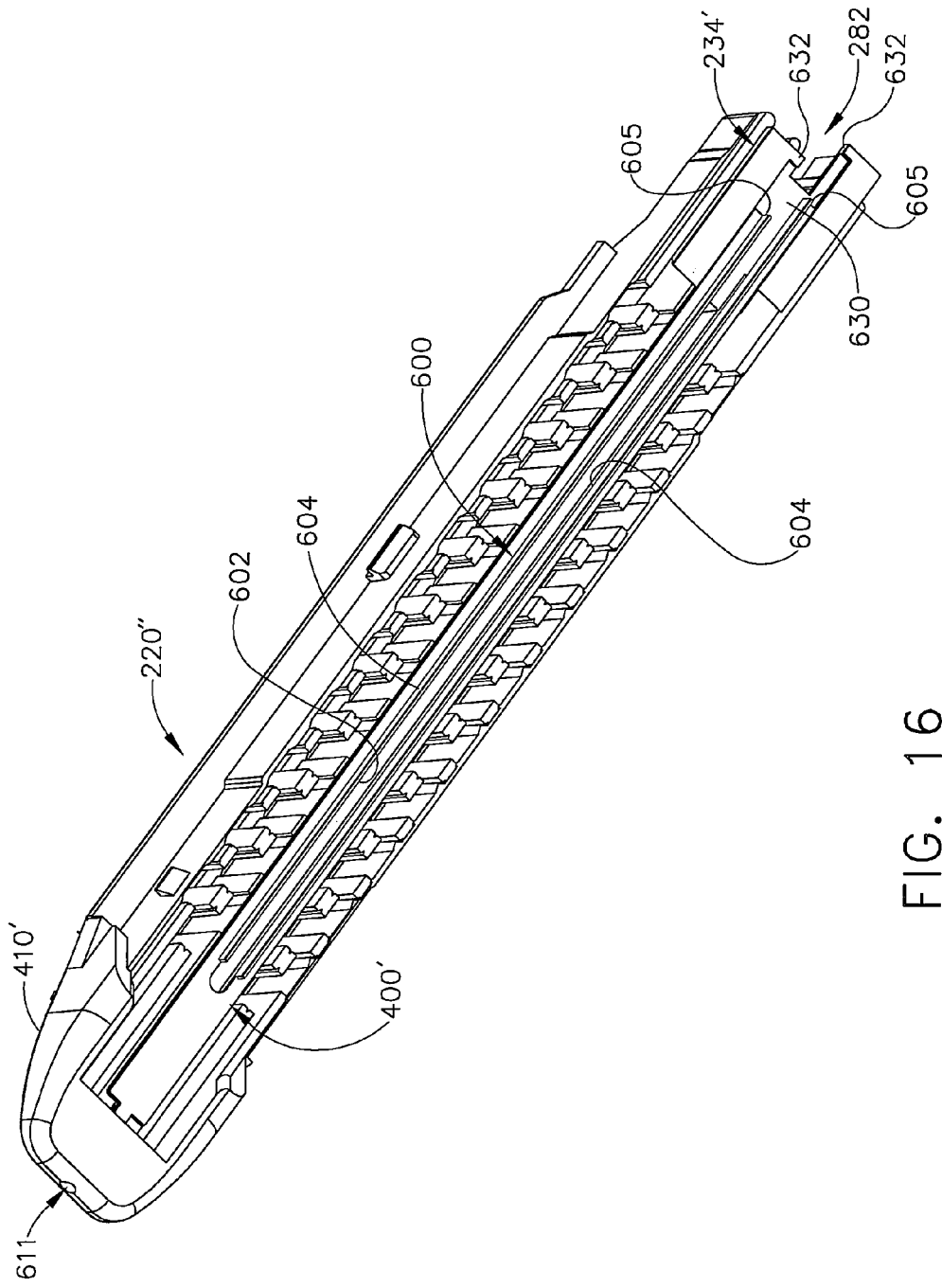
FIG. 16 is a bottom perspective view of a portion of a staple cartridge embodiment of the present invention.
Figure 17:
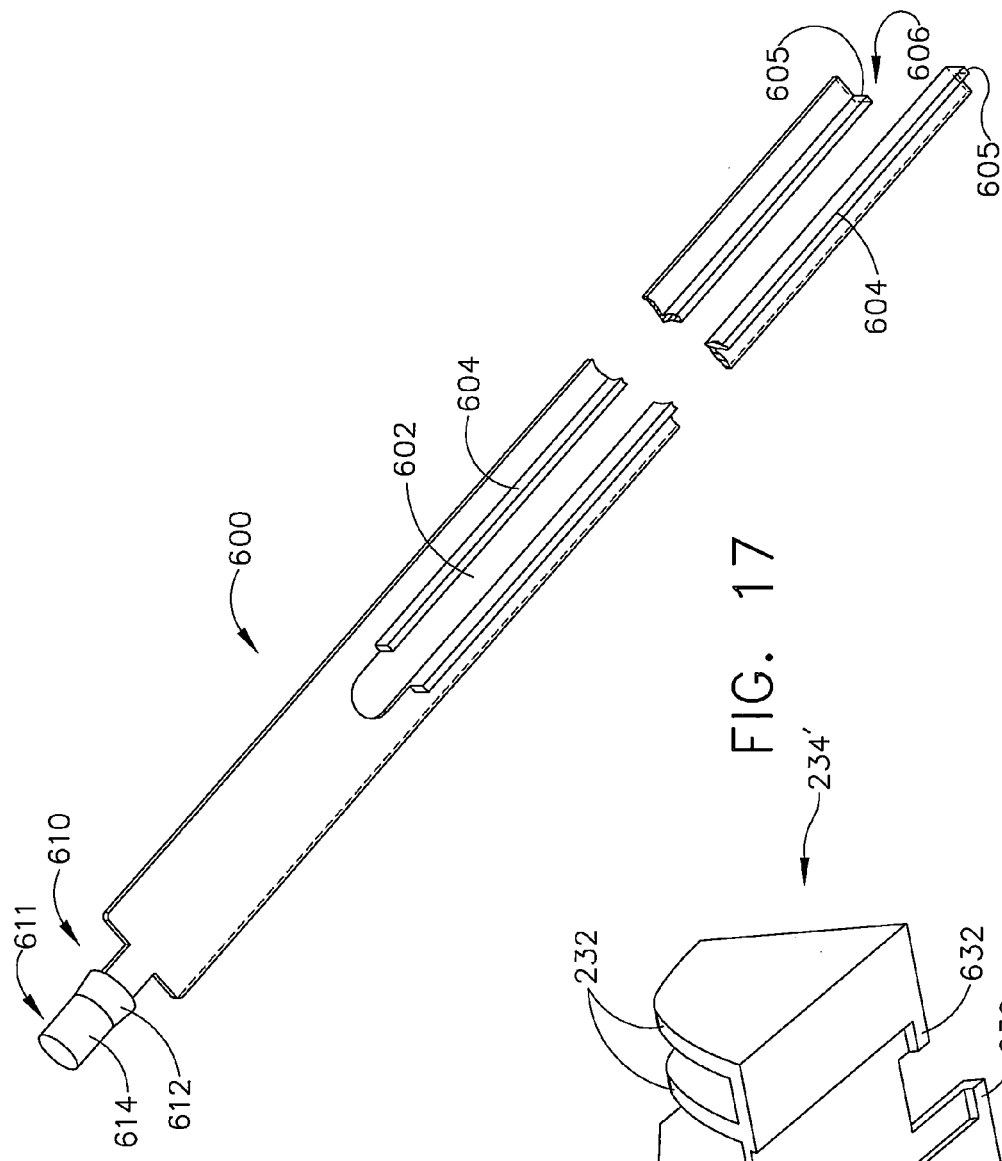
FIG. 17 is a partial perspective view of an indicator base embodiment of the present invention.
Figure 18:
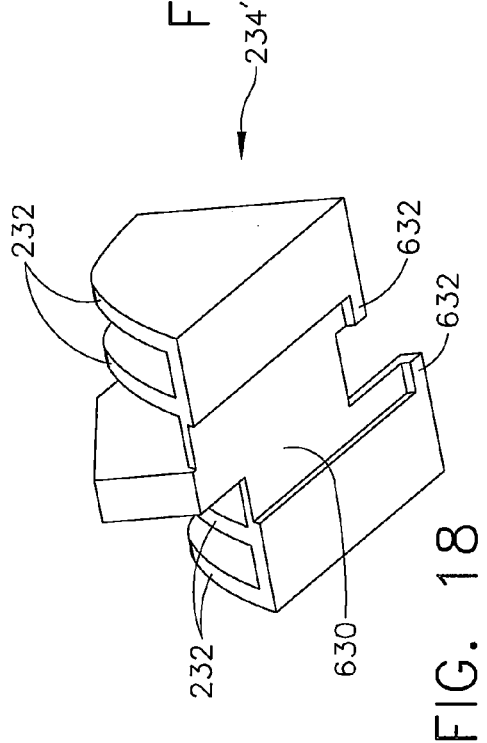
FIG. 18 is a bottom perspective view of an actuation sled embodiment of the present invention.

In various embodiments, the spent cartridge indication system 400' may comprise an indicator base 600 that is movably supported within the tool assembly 17 as shown in FIG. 16. The indicator base 600 may have a longitudinal slot 602 therein that enables the vertical support strut 278 of the axial drive assembly 212 to pass therethrough. In addition, the indicator base 600 may have a pair of stiffening rails 604 protruding therefrom. In various embodiments, for example, the indicator base 600 may be stamped from metal or otherwise fabricated from other suitable materials. As can be seen in FIG. 17, the proximal end 606 of the indicator base 600 may be staggered to accommodate the staggered wedges 232 of the actuation sled 234'. The proximal end 606 of the indicator base 600 is adapted to be received in a recess 630 formed in the bottom of the actuation sled 234'. See FIG. 18. As can also be seen in FIG. 18, a pair of shear stops 632 are formed in the bottom of the actuation sled 234' to engage the distal end 606 of the indicator base 600. More specifically to engage the distal ends 605 of the stiffening rails 604.

The distal end 610 of the indicator base 600 has a spent cartridge indicator pin 611 protruding distally therefrom. The indicator pin 611 may have a distal portion 614 and a locking cone portion 612. The distal portion 614 is sized to be slidably received in a hole 414' provided in the distal end 410' of the staple cartridge 220". Hole 414' further has a tapered portion 415' that is oriented to engage the locking cone portion 612 as will be discussed below.

Figure 19:
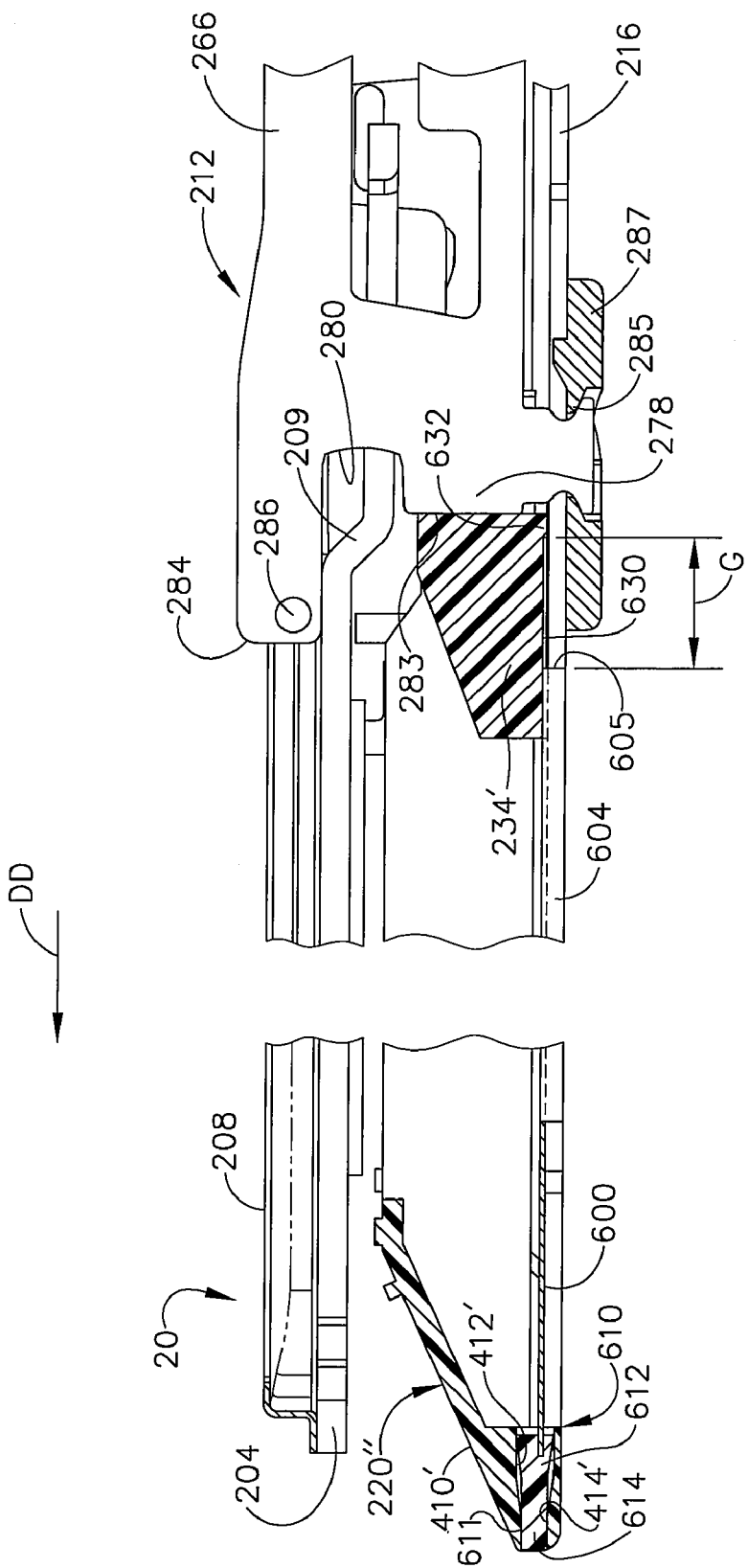
FIG. 19 is a side cross-sectional view of a portion of a disposable loading unit embodiment of the present invention with some components shown in full view for clarity and wherein the disposable loading is in an unfired position.
Figure 23:
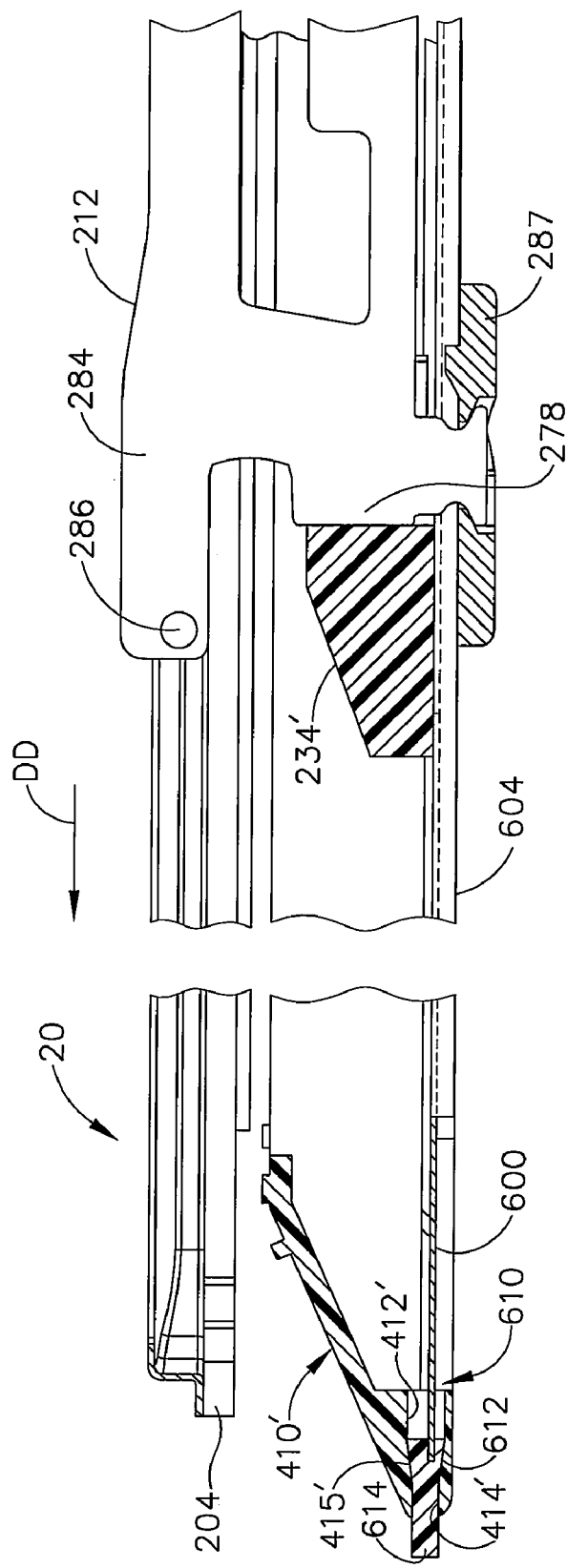
FIG. 23 is a side cross-sectional view of a portion of a disposable loading unit embodiment of the present invention during a firing stroke with some components shown in full view for clarity.

As can be seen in FIGS. 16 and 19, when the staple cartridge 220" is in the unfired position, distal end 610 of the indicator base 600 is received within the recess 630 in the actuation sled 234'. A camming surface 209 is formed on a proximal end of anvil portion 204 and is positioned to engage axial drive assembly 212 to facilitate closing of the anvil assembly 20. See FIG. 19. As is discussed in U.S. Pat. No. 5,865,361, the anvil assembly 20 is closed by driving the axial drive assembly 212 in the distal direction "DD" such that the camming pin 286 engages the camming surface 209 and pivots the anvil assembly 20 closed. Often times during a procedure, however, the clinician must open and close the anvil assembly 20 multiple times to manipulate tissue and to grasp and clamp the target tissue between the anvil assembly 20 and the staple cartridge 220". Thus, the anvil assembly 20 may be opened and closed several times before the clinician desires to commence the firing process. In various embodiments, therefore, to avoid actuation of the indicator system 400' during the opening and closing actions, a gap "G" is provided between the shear stops 632 and the corresponding proximal ends 605 of the stiffening rails 602. See FIG. 20. It will be understood that the gap "G" facilitates movement of the axial drive assembly 212 and actuation sled 234' in the distal direction "DD" a sufficient distance to cause the anvil assembly 20 to pivot closed without distally advancing the indicator base 600 from a "prefired" position (FIGS. 19 and 20) to a "fired" position (FIG. 23).

Figure 20:
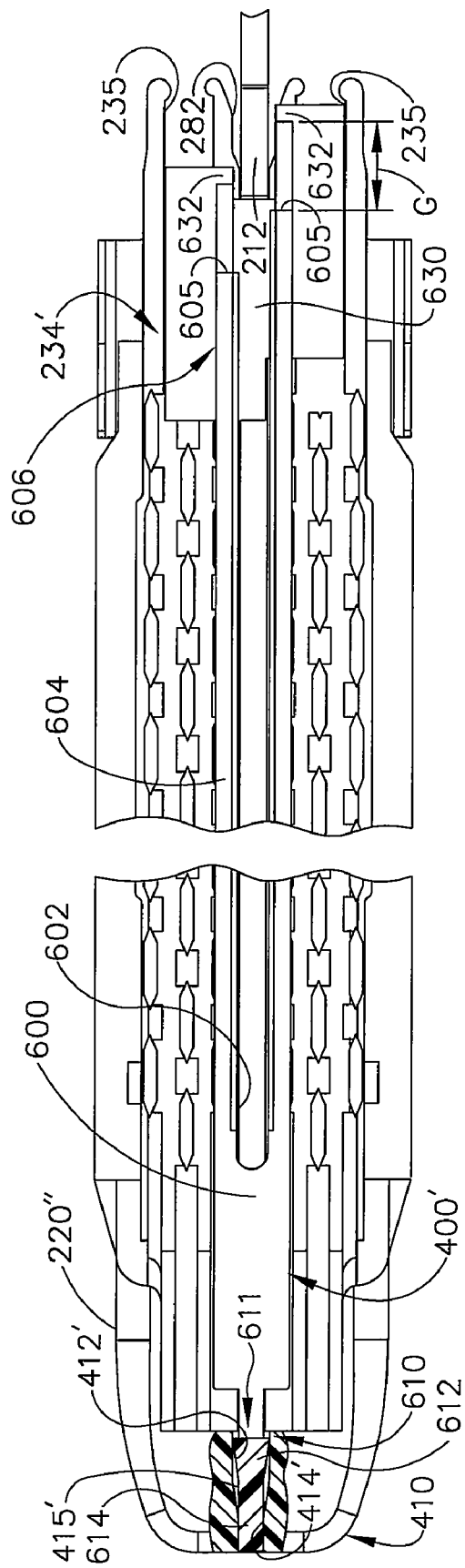
FIG. 20 is a bottom plan view of the surgical staple cartridge of the disposable loading unit of FIG. 19.
Figure 22:
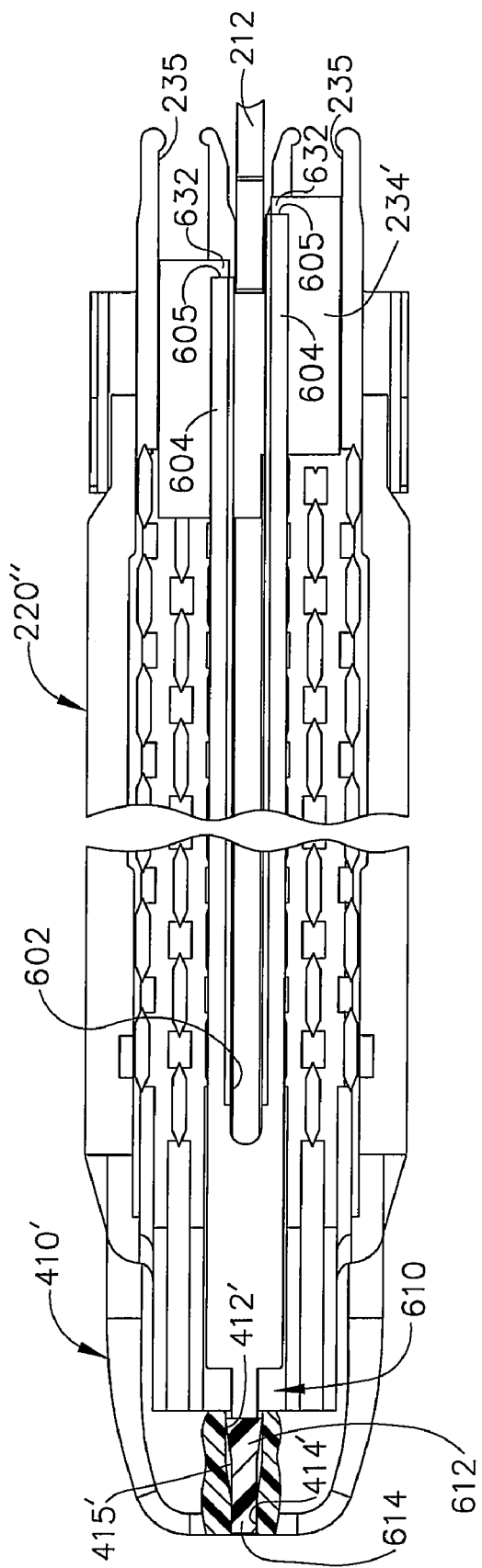
FIG. 22 is a bottom plan view of the surgical staple cartridge of FIG. 21.
Figure 24:
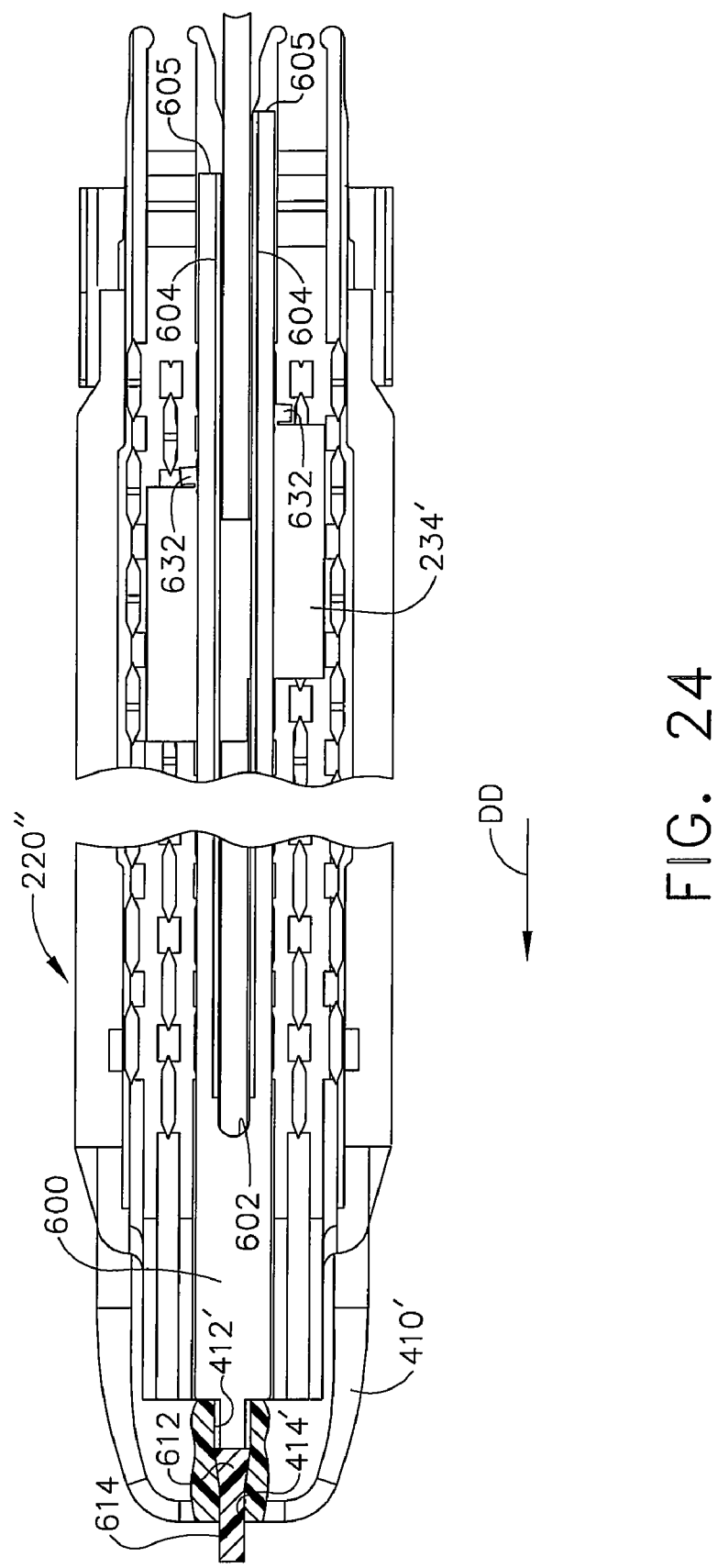
FIG. 24 is a bottom plan view of the surgical staple cartridge of FIG. 23.
Figure 25:
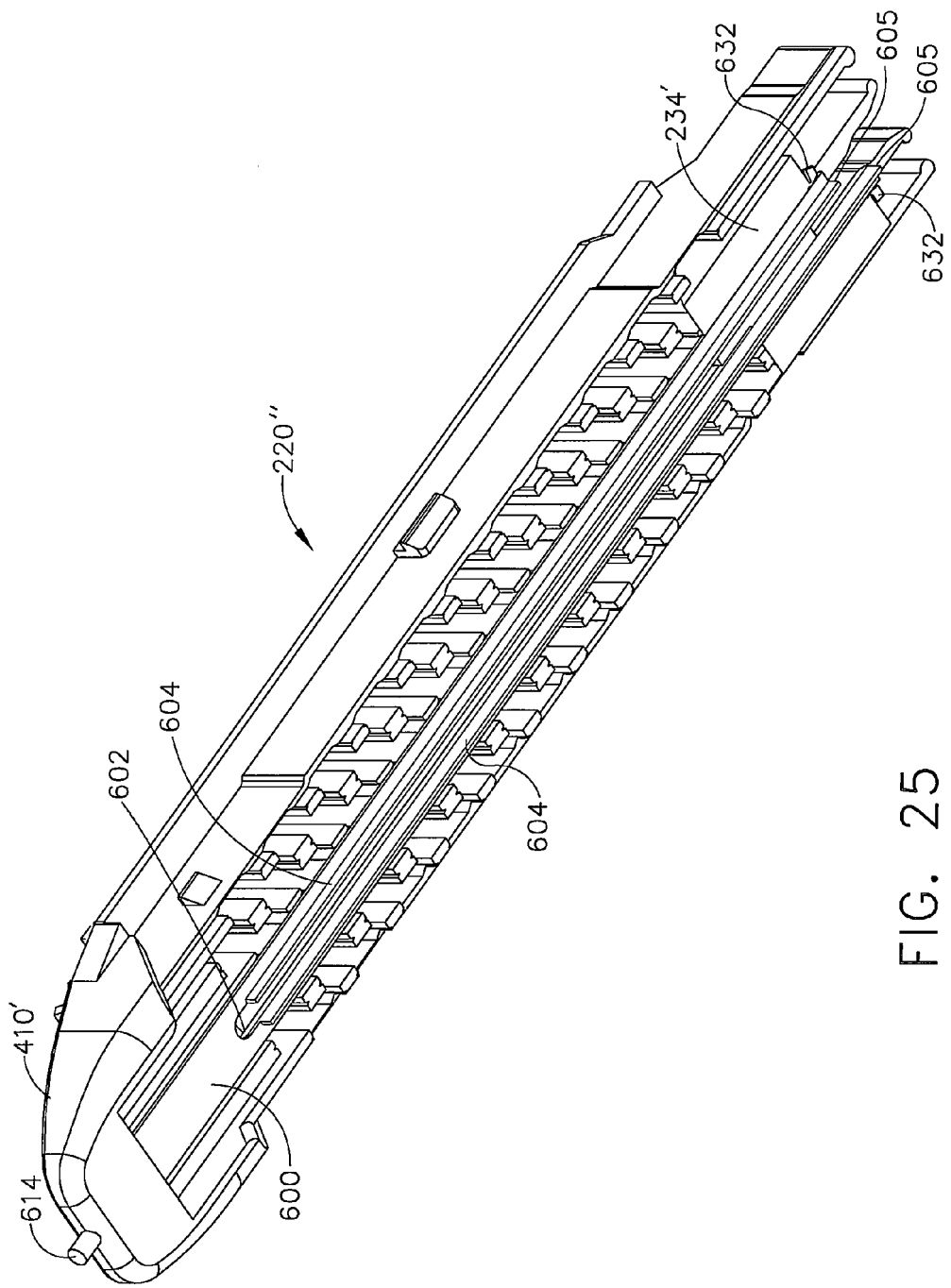
FIG. 25 is a bottom perspective view of the surgical staple cartridge of FIG. 24 wherein the spent cartridge indicator pin has been extended indicating that the disposable loading unit has been fired.

Operation of the spent cartridge indication system 400' will now be described with reference to FIGS. 19-25. FIGS. 19 and 20 illustrate the position of the indicator base 600 and the actuation sled 234' prior to closing the anvil assembly 20. FIGS. 21 and 22 illustrate the positions of the indicator base 600 and the actuation sled 234' after the axial drive assembly 212 has been advanced distally to close the anvil assembly 20. As can be seen in those Figures, the proximal ends 605 of the stiffening bars 602 are adjacent to their corresponding shear stops 632. FIGS. 23 and 24 illustrate the positions of the indicator base 600 and the actuation sled 234' after the firing sequence has commenced. As can be seen in those Figures, as the axial drive assembly 212 is driven in the distal direction "DD", the shear stops 632 contact the distal ends 605 of the stabilizing bars 602 on the indicator base 600 driving the indicator base 600 in the distal direction "DD" such that the indicator pin portion 614 protrudes out of the hole portion 414' and the locking cone portion 612 engages the tapered hole portion 415' in the staple cartridge nose 410'. After the locking cone portion 612 becomes seated in the tapered hole portion 415', further advancement of the axial drive assembly 212 in the distal direction "DD" causes the shear stops 632 to shear off of the actuation sled 234' (or move to an orientation that permits the actuation sled 234' to continue to move distally relative to the indication base 600). See FIGS. 24 and 25. Thus, the indicator pin 614 of the indicator base 600 will be pushed out of the distal end 410' of the staple cartridge 220" and retained there to indicate to the clinician that the staple cartridge 220" has been spent or previously fired. Such arrangement enables the clinician to quickly determine whether the disposable loading unit 516 has been previously fired. Those of ordinary skill in the art will appreciate that the unique and novel spent cartridge indication system may be effectively employed in connection with articulatable and non-articulatable disposable loading units alike.

Figure 26:
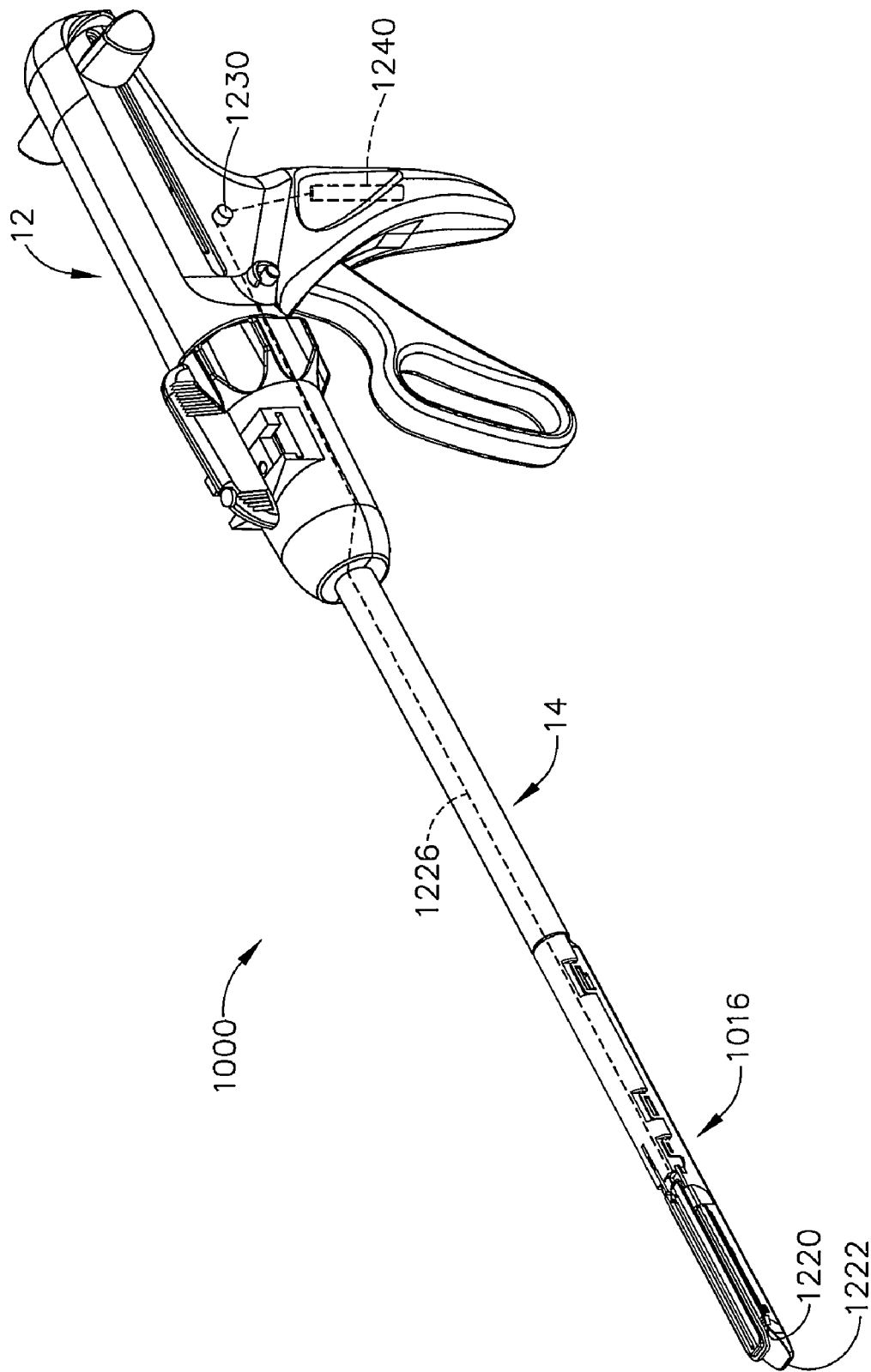
FIG. 26 is a perspective view of a surgical stapling apparatus embodiment of the present invention.
Figure 27:
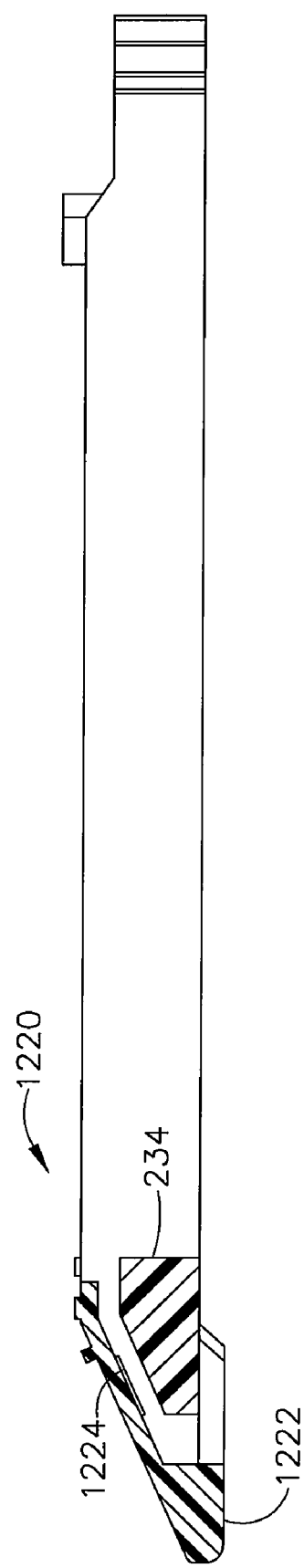
FIG. 27 is a partial cross-sectional view of a surgical staple cartridge of an embodiment of the present invention with some of the components thereof omitted for clarity.

FIG. 26 illustrates a surgical stapling apparatus embodiment 1000 of the present invention that has a disposable loading unit 1016 embodiment of the present invention coupled thereto. The surgical stapling apparatus 1000 may comprise a handle assembly 12 that has an elongated body 14 protruding therefrom. The handle assembly 12 and the elongated body 14, as well as the components that make up such elements, may generally operate in the manner discussed in U.S. Pat. No. 5,865,361, except for the differences discussed below. In this embodiment, the disposable loading unit 1016 employs a surgical staple cartridge 1220. The surgical staple cartridge embodiment 1220 may be substantially similar to surgical staple cartridge 220 described above, except for the improvements discussed below. In particular, as illustrated in FIG. 27, in this embodiment, a conventional switch 1224 (e.g., pressure switch, magnetic switch, etc.) may be positioned within the distal end 1222 such that when the actuation member or sled 234 contacts the switch 1224 or comes into close proximity therewith, a signal is transmitted through a wire or wires 1226 to an indicator 1230 mounted in the handle assembly 12. A power source 1240, such a battery, may be mounted in the handle assembly 12 and be coupled to the switch 1224, such that when the switch 1224 is activated, power is permitted to travel from the power source 1240 through the switch 1224 to the indicator 1230. The indicator 1230 may comprise a light or other suitable indication means to indicate to the clinician that the disposable loading unit 1016 has been fired. Those of ordinary skill in the art will appreciate that the staple cartridge 1220 embodiment may be effectively employed in connection with articulatable and non-articulatable disposable loading units alike without departing from the spirit and scope of the present invention.

Figure 28:
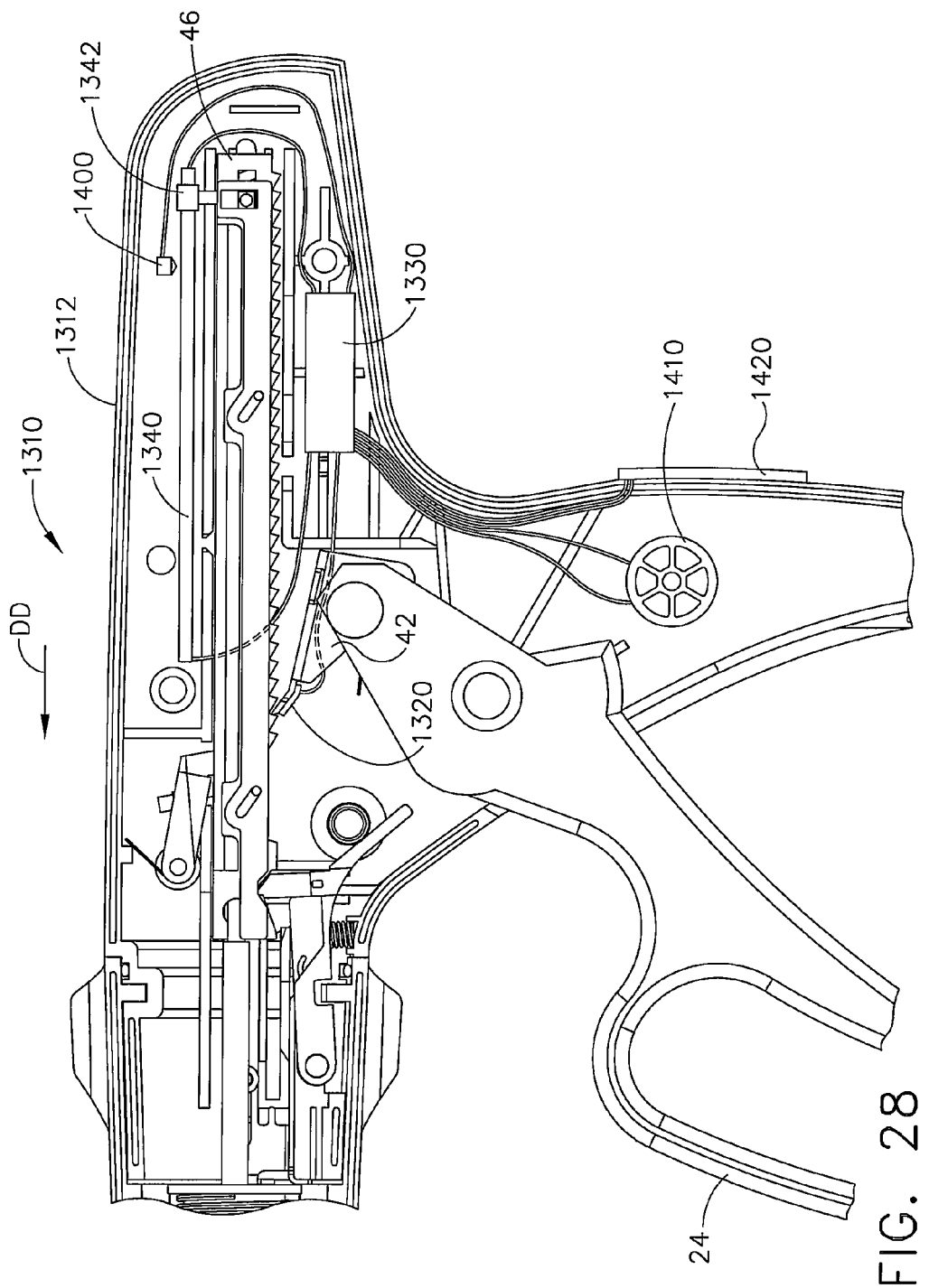
FIG. 28 is a side view of the interior of a handle assembly of a surgical stapling apparatus embodiment of the present invention.
Figure 29:
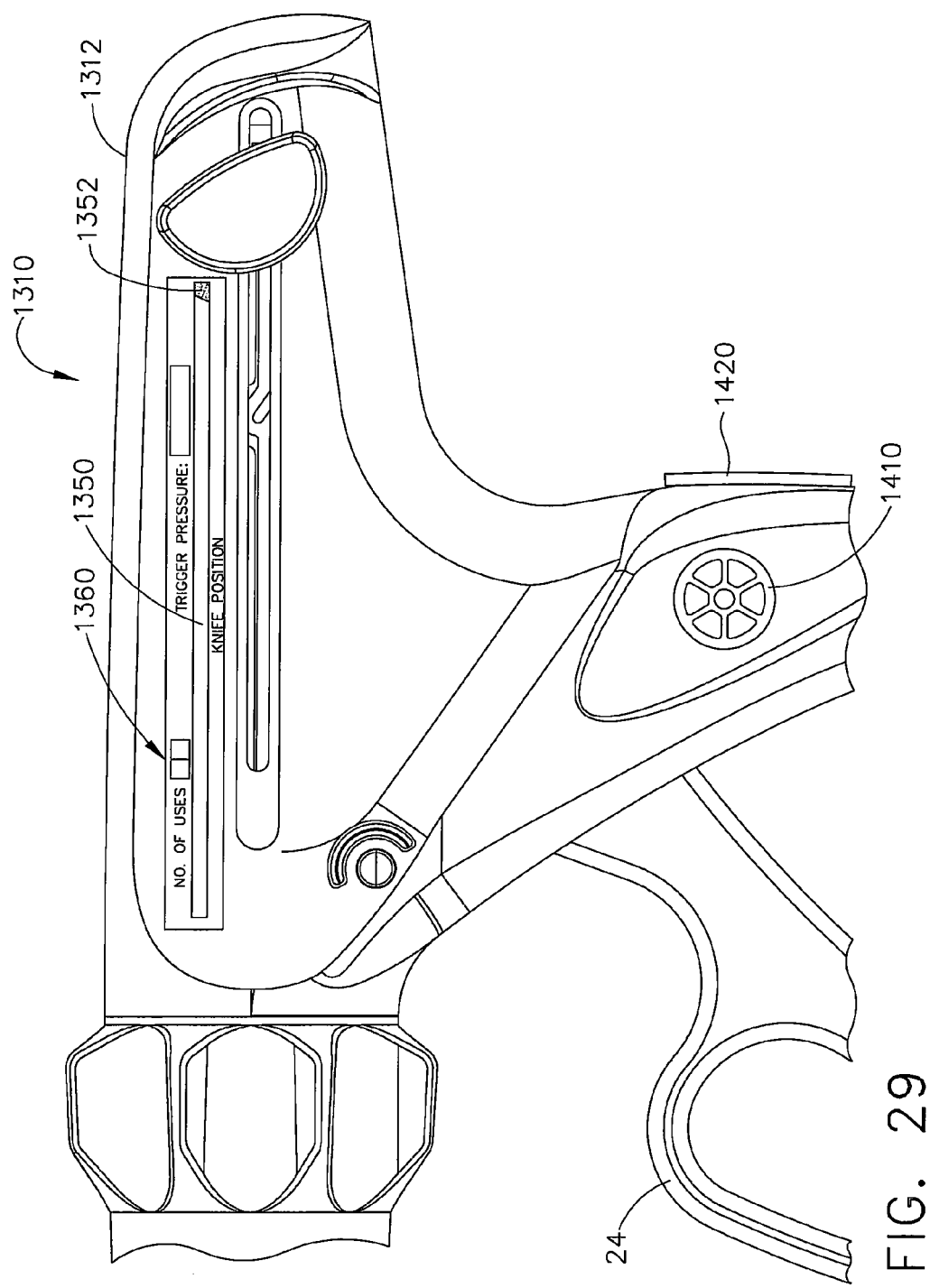
FIG. 29 is a side view of the handle assembly of FIG. 28.

FIGS. 28 and 29 illustrate another surgical stapling apparatus embodiment 1310 of the present invention that has a handle assembly 1312. The construction and operation of various components located within the handle assembly 1312 are discussed in U.S. Pat. No. 5,865,361. In addition to those components, the handle assembly 1312 of the present invention includes a first strain gauge 1320 that operably interfaces with the driving pawl 42 that engages the toothed rack 48 on the actuation shaft 46. The first strain gauge 1320 is electrically coupled to a processor 1330 that receives the inputs form the first strain gauge 1320 and calculates an amount of trigger pressure in pounds per square inch (PSI) associated with each activation of the movable handle 24. The processor displays the calculated trigger pressure on a trigger pressure display 1322 mounted in the handle assembly 1312. See FIG. 29.

The handle assembly 1312 may further support an impedance bar 1340 and a displacement encoder 1342 that is constrained to move on or adjacent to the impedance bar 1340. In various embodiments, for example, the encoder 1342 may be mounted to a proximal end of the actuation shaft 46 for travel therewith. Thus, as the actuation shaft 46 is advanced in the distal direction "DD" (which results from ratcheting the movable handle portion 24 as discussed in U.S. Pat. No. 5,865, 361), the signals from the encoder 1342 are communicated to the processor 1330. A first switch 1400 may be mounted relative to the impedance bar 1340 such that as the actuation shaft 46 is moved distally a distance required to close the anvil assembly 20, the first switch 1400 may be triggered by the encoder 1342 or other trigger arrangement mounted to the actuation shaft 46. The first switch 1400 may be electrically coupled to the processor 1300 which may be coupled to an indicator light (not shown), a speaker 1410 and/or a vibrator 1420 mounted on the handle assembly 1312. Thus, when the anvil assembly 20 has been moved to a closed position, the processor 1300 may provide the user with an indication in the form of a sound through the speaker 1410 and or vibration motion through vibrator 1420.

As can be seen in FIG. 29, the handle assembly 1312 may also include a light screen or light emitting diode screen 1350. As the actuation shaft 46 is driven in the distal direction "DD" during the firing of the apparatus 1310, the light band 1352 on the screen 1350 will grow in the distal direction. The clinician can then determine the position of the actuation shaft 46 during the firing process based upon how far the light band 1352 extends distally on the screen 1350. Thus, when the actuation shaft 46 has been moved to its distal-most position and the disposable loading unit coupled thereto has been completely fired, the light band 1352 may extend completely across the screen 1350. Utilizing the input from the encoder 1342, the processor 1330 may also calculate the number of times that the handle assembly 12 has been fired and display that information on a display 1360. See FIG. 29.

Figure 30:
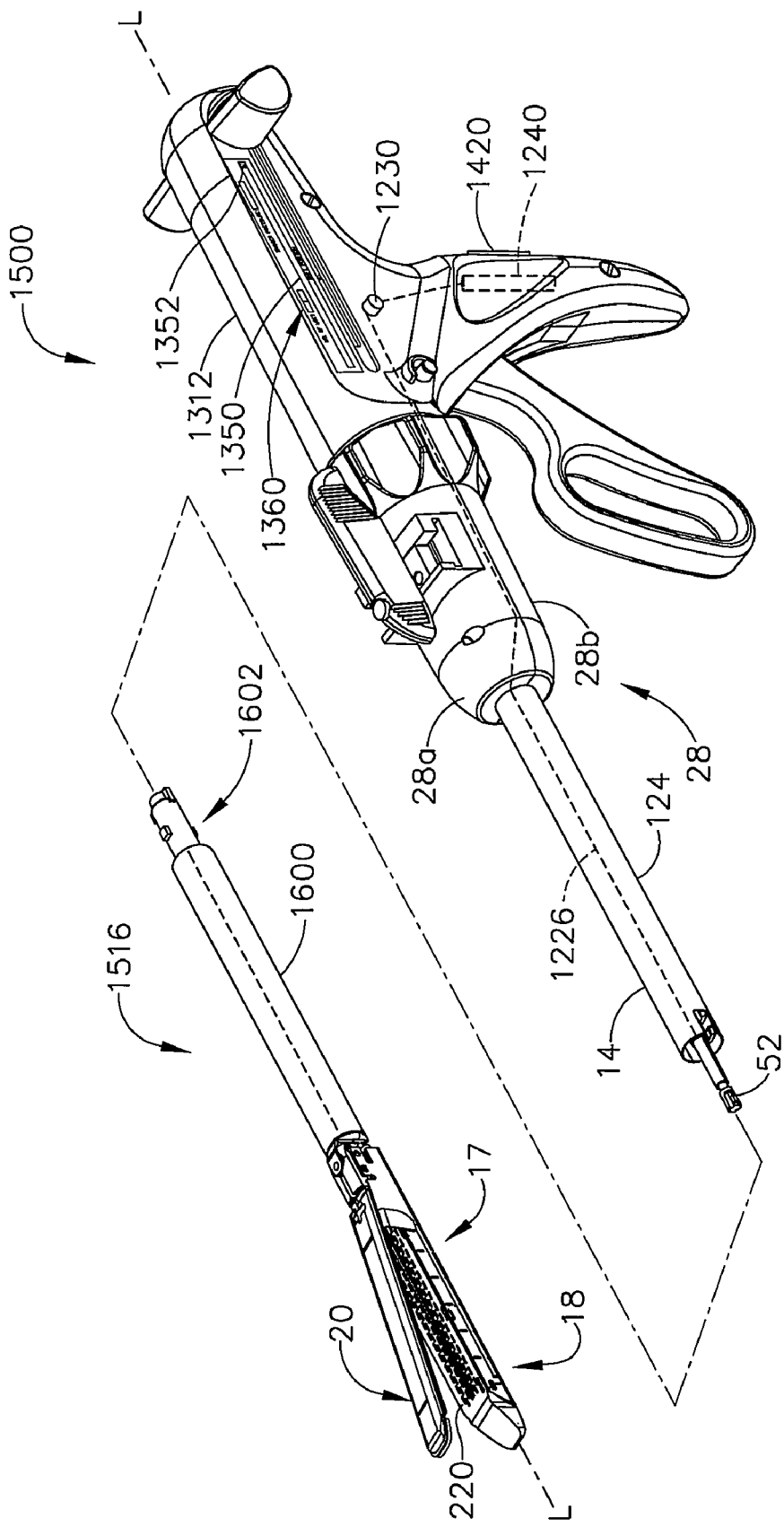
FIG. 30 is a perspective view of a surgical stapling apparatus embodiment of the present invention.

FIGS. 30-36 illustrate another surgical stapling instrument embodiment 1500 that is equipped with a blade monitoring system 1700 of the present invention. As can be seen in FIG. 30, the surgical stapling instrument 1500 may include a handle assembly 1312 of the type and construction described above with the blade monitoring system 1700 of the present invention incorporated therein. As can also be seen in FIG. 30, the surgical stapling instrument 1500 may include a disposable loading unit 1516 that is constructed for removable attachment to the elongated body 14 that protrudes from the handle assembly 12. The disposable loading unit 1516 may generally comprise a tool assembly 17 for performing surgical procedures such as cutting tissue and applying staples on each side of the cut. The tool assembly 17 may include a cartridge assembly 18 that houses a plurality of surgical staples therein. The tool assembly 17 may also include a staple-forming anvil assembly 20 of the type and construction described above. The disposable loading unit 1516 may also include an axial drive assembly 1512 that may have the attributes of the axial drive assembly described in U.S. Pat. No. 5,865,361 with the improvements described below.

In various embodiments for example, the axial drive assembly 1512 comprises a drive beam 1566. As can be seen in FIG. 32, the distal end of drive beam 1566 may include a vertical support strut 1578 which supports the knife blade 1580, and an abutment surface 1583. A retention flange 1584 may project distally from vertical strut 1578 and support a camming pin 1586 at its distal end. Camming pin 1586 may be dimensioned and configured to engage a camming surface on the anvil assembly 20 to clamp the anvil assembly 20 against body tissue in a known manner. The drive beam 1566 may be constructed from a single sheet of material or, preferably, from multiple stacked sheets and have an engagement end 1570. Engagement end 1570 may include a pair of engagement fingers 1570a and 1570b which may be dimensioned and configured to mountingly engage a pair of corresponding retention slots formed in drive member as is known. The drive member facilitates interconnection of the drive beam 1566 to a control rod 52 when the proximal end of disposable loading unit 1516 is coupled to the elongated body 14 of the surgical stapling apparatus 1500.

The disposable loading unit 1516 may further include a housing assembly 1600 that may comprise an upper housing segment 1610 and a lower housing segment 1620 that are interconnected together to form the housing portion 1600. The upper housing segment 1610 and the lower housing segment 1620 may be interconnected by adhesive, snap features, fasteners, etc. As can be seen in FIG. 33, the upper housing segment 1610 may have an elongate groove 1612 therein to receive a portion of the drive beam 1566 therein. Likewise, the lower housing segment 1620 may have an elongate groove 1622 therein for receiving a portion of the drive beam 1566 therein.

As can be most particularly seen in FIG. 32, the blade monitoring system 1700 may comprise a strain gage 1710 that is mounted to the vertical strut portion 1578 adjacent the blade 1580. The strain gage 1710 may have a pair of gage leads 1712 that extend along the drive beam 1566 and terminate in interface terminals 1714 adjacent the engagement end 1570 of the drive beam 1566. The gage leads 1712 are arranged for electrical contact with conductive traces 1614 and 1624 in the housing segments 1610 and 1620, respectively, when the drive beam 1566 is received within the elongate grooves 1612 and 1622. As can be seen in FIGS. 33 and 34, the conductive trace 1614 terminates in an upper reload terminal 1616 provided on a proximal end portion 1602 of the housing 1600. Likewise, the conductive trace 1624 terminates in a lower reload terminal 1626 provided on the proximal end portion 1602 of the housing 1600.

Figure 35:
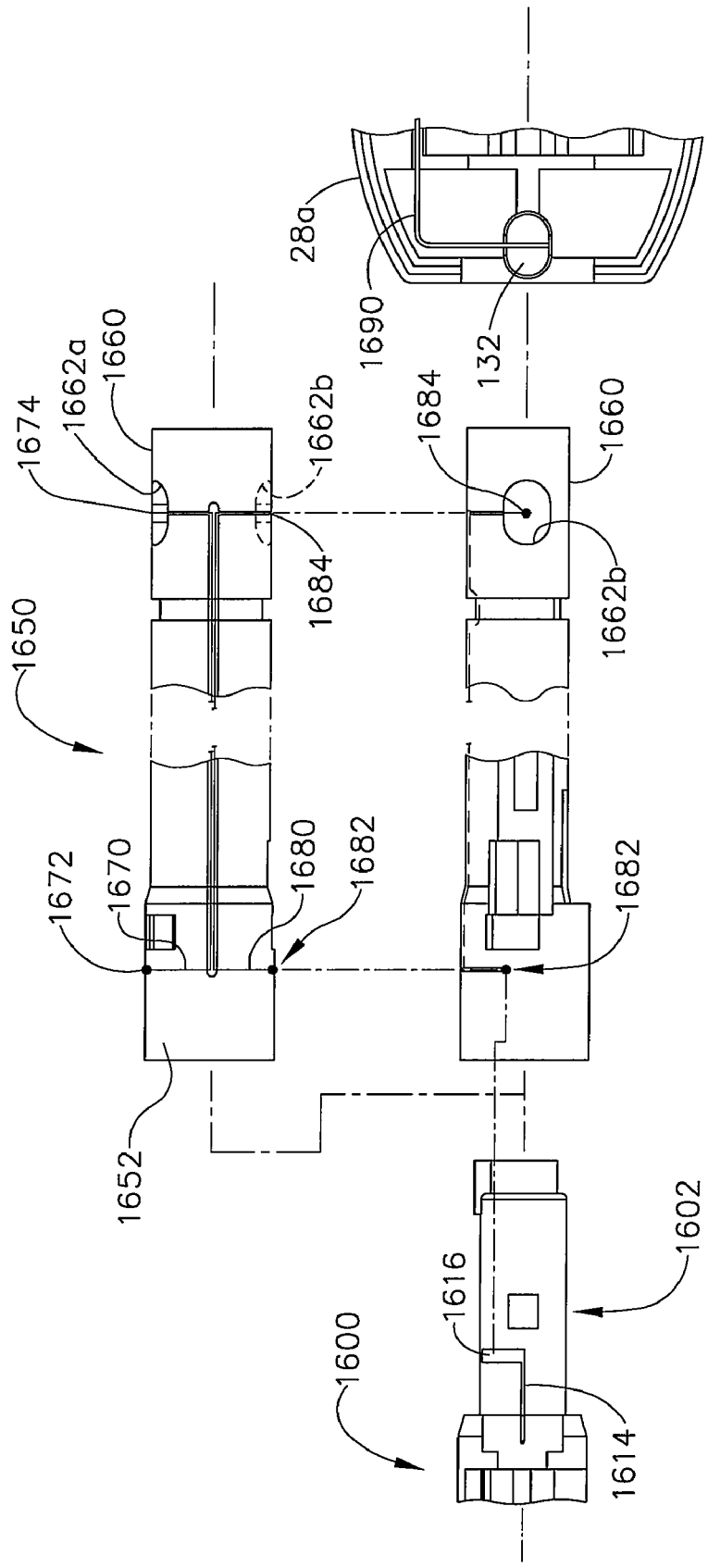
FIG. 35 is an exploded assembly view of a portion of a disposable loading unit and a data transmission body and a portion of a rotatable knob of an embodiment of the present invention with two orientations of the data transmission body shown for clarity.
Figure 36:
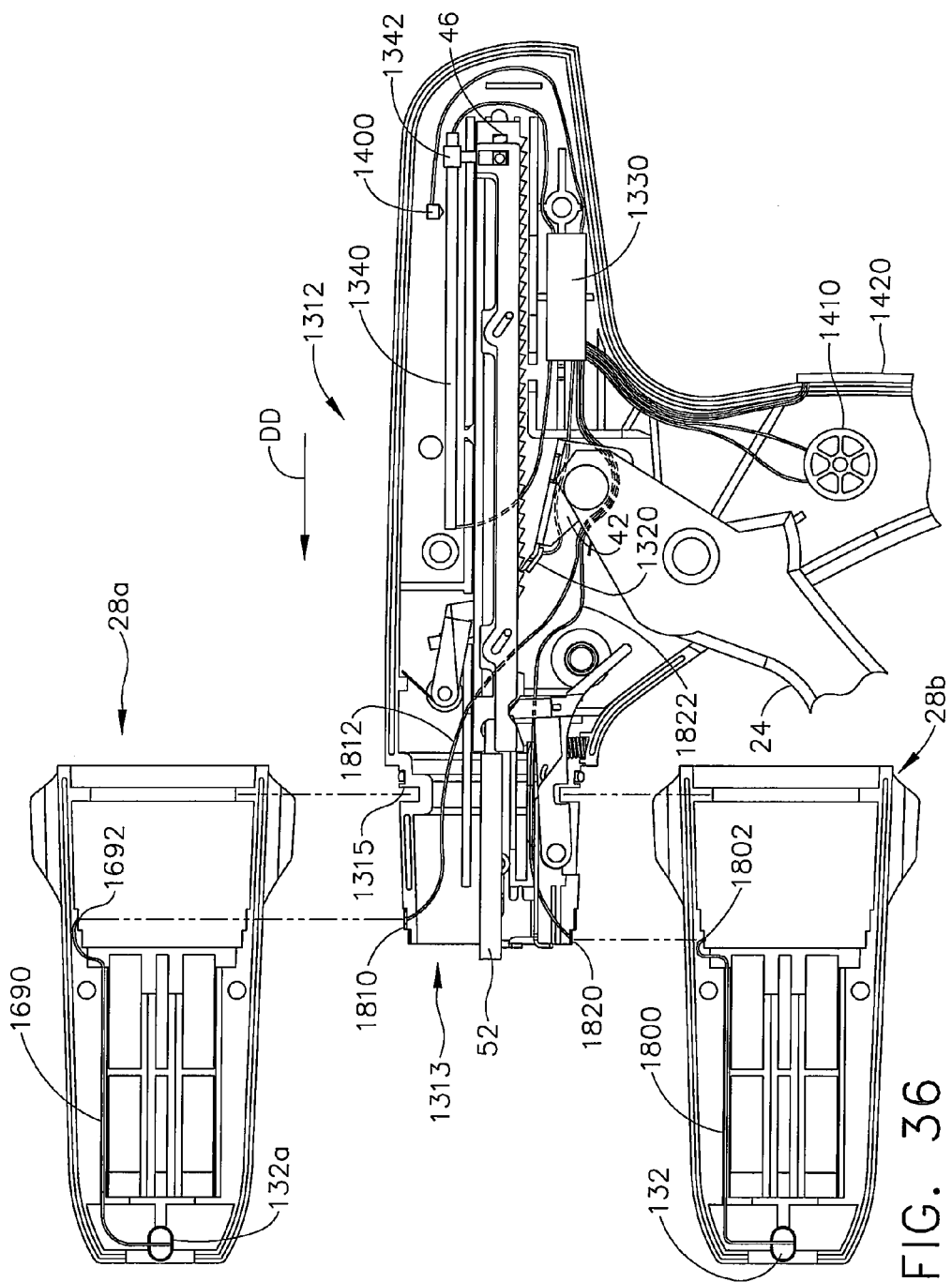
FIG. 36 is an exploded assembly view of a rotatable knob and a portion of a handle assembly of an embodiment of the present invention.

In various embodiments, the elongated body 14 supports a data transmission body 1650 which is configured to operably support the control rod 52 therein. As can be seen in FIG. 35, the data transmission body 1650 may have a distal end 1652 that is configured for removable attachment with the proximal end 1602 of the housing 1600 similar to the bayonet-type connection described in U.S. Pat. No. 5,865,361. As can be seen in FIGS. 30 and 36 a rotatable knob 28 may be mounted on the forward end of the handle assembly 1312 to facilitate rotation of elongated body 14 with respect to handle assembly 1312 about longitudinal axis "L-L" of the stapling apparatus 1500. The rotatable knob 28 may be formed from knob segments 28a and 28b that are fastened together by snap features, adhesive, fasteners, etc. The knob segments 28a and 28b each may have a radial projection 132 formed thereon that is adapted to extend into corresponding openings (not show) in an outer casing 124 of the elongated body 14 and into depressions 1662a, 1662b in a proximal end 1660 of the data transmission body 1650. Projections 132 fixedly secure rotation knob 28 and the elongated body 14 in relation to each other, both longitudinally and rotatably. Rotation of rotation knob 28 with respect to handle assembly 1312 thus results in corresponding rotation of elongated body 14 about longitudinal axis L-L with respect to handle assembly 1312. It will also be appreciated that because the disposable loading unit 1516 is coupled to the distal end of the elongated body 14, rotation of the elongated body 14 also results in the rotation of the disposable loading unit 1516.

As can be seen in FIG. 35, the data transmission body 1650 has a right data lead 1670 that penetrates through the distal end 1652 to form a lower body penetration 1672 that is oriented for electrical contact with the lower reload terminal 1626 when the proximal end 1602 of the housing 1600 is coupled to the distal end 1652 of the data transmission body 1650. Likewise, the data transmission body 1650 further has a left data lead 1680 that penetrates through the distal end 1652 to form an upper body penetration 1682 that is oriented for electrical contact with the upper reload terminal 1616 when the proximal end 1602 of the housing 1600 is coupled to the distal end 1652 of the data transmission body 1650. The right data lead 1670 extends through the data transmission body 1650 and terminates in mounting depression 1662a to form a right termination end 1674 and the left data lead 1680 extends through the data transmission body 1650 and terminates in the other mounting depression 1662b to form a left terminal end 1684. See FIG. 35.

As can be further seen in FIGS. 35 and 36, the right knob segment 28a has a right hand shroud lead 1690 supported therein that terminates at a proximal right terminal end 1692. The right hand shroud lead 1690 also terminates through the projection 132 formed in the right hand knob segment 28a such that when the projection 132a extends into the depression 1662a in the proximal end 1660 of the data transmission body 1650, an electrical connection is formed between the right hand shroud lead 1690 and the right termination end 1664. Likewise, the left hand knob segment 28b has a left hand shroud lead 1700 supported therein that terminates at a proximal left terminal end 1702. The left hand shroud lead 1700 also terminates through the projection 132b formed in the left hand knob segment 28b such that when the projection 132b extends into the depression 1662, an electrical connection is formed between the left hand shroud lead 1700 and the left termination end 1684.

In various embodiments, the distal end portion 1313 of the handle assembly 1312 has a right conductive annular band 1810 thereon which is connected to the processor 1330 by a lead 1812 and a left conductive annular band 1820 which is also connected to the processor by a lead 1822. The right knob segment 28a has an inwardly extending attachment flange portion 29a formed thereon adapted to be received in an annular groove 1315 formed in the distal end 1313 of the handle assembly 1312. Similarly, the left knob segment 28b has an inwardly extending attachment flange portion 29b formed thereon adapted to be received in the annular groove 1315. Thus, when the right knob segment 28a is coupled to the left knob segment 28b (by adhesive, snap features, fasteners, etc., the attachment flange portions 29a, 29b serve to retain the knob 28 on the housing 1312 while facilitating rotational travel of the knob 28 relative thereto. In addition, when the knob 28 is rotatably supported on the handle assembly 1312, the right terminal end is in electrical contact with the right conductive annular band 1810 and the left terminal end is in electrical contact with the left conductive annular band 1820. Thus, when the disposable loading unit 1516 is coupled to the elongate body 14, electrical connections are established between the strain gage and the processor 1330.

As the axial drive assembly 1512 is driven distally through tissue clamped in the tool assembly 17, the blade 1580 will experience forces "F" the magnitude of which may depend upon the amount of tissue clamped in the tool assembly 17. See FIG. 32. Such forces "F" will tend to elongate the vertical support strut 1578 which supports the knife blade 1580. As the forces "F" are applied to the vertical support strut 1578, the strain gauge 1710 will detect an amount of strain experienced by the vertical support strut 1578 and communication such data to the processor 1330. The processor 1330 then manipulate the strain data in a known manner and transmits the data on a display 1322 mounted in the handle assembly 1312. In other embodiments, the processor 1330 can activate the vibrator 1420 to cause the vibrations of the vibrator to increase as the amount of strain experienced by the vertical support strut 1578 and the blade 1580 increase.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A disposable loading unit for attachment to a surgical stapling apparatus, said disposable loading unit comprising:
    a carrier;
    a staple cartridge supported in said carrier;
    an anvil assembly movably coupled to said carrier for selective movable travel between open and closed positions relative to said staple cartridge;
    an axial drive assembly having a distal end portion constructed to move in a distal direction from a start position to an end position through said staple cartridge in response to a drive motion imparted to said axial drive assembly from the surgical stapling apparatus, said axial drive assembly having a firing indicator region spaced from said distal end thereof; and
    a housing coupled to said carrier and configured for operable attachment to the surgical stapling apparatus, said housing having a distal end and an axially extending opening therein spaced from said distal end thereof such that said firing indicator region is observable through said axially extending opening;
    as said axial drive assembly is driven from said start position to said end position.

2. The disposable loading unit of claim 1 wherein said firing indicator region of said axial drive assembly has a color that differs from a color of said housing.

3. The disposable loading unit of claim 1 further comprising a firing indicator assembly associated with said carrier.

4. The disposable loading unit of claim 3 wherein said firing indicator assembly comprises an elongate slot through said carrier to permit another portion of said axial drive assembly to be observed as said axial drive assembly is driven from said start position to said end position.

5. The disposable loading unit of claim 1 further comprising a transparent window covering said axially extending opening in said housing.

6. The disposable loading unit of claim 1 wherein a said firing indicator region of said axial drive assembly protrudes out of said axially extending opening in said housing.

7. The disposable loading unit of claim 1 further comprising
    a second axially extending opening through said housing such that a second portion of said axial drive assembly is viewable therethrough.

8. The disposable loading unit of claim 1 further comprising a firing scale adjacent said axially extending opening in said housing.

9. The disposable loading unit of claim 8 wherein said firing scale comprises indicia selected from the group of indicia consisting of numbers, letters, colors and combinations of numbers letters and colors.

10. A disposable loading unit for attachment to a surgical stapling apparatus, said disposable loading unit comprising:
    a staple cartridge supported in a carrier operably couplable to the surgical stapling apparatus;
    an anvil assembly movably coupled to said carrier for selective movable travel between open and closed positions relative to said staple cartridge;
    an axial drive assembly having a distal end portion constructed to move in a distal direction from a start position to an end position through said staple cartridge in response to a drive motion imparted to said axial drive assembly from the surgical stapling apparatus;
    a housing coupled to said carrier and configured for operable attachment to the surgical stapling apparatus; and
    a firing indicator movably supported on said housing for contact by a portion of said axial drive assembly as said axial drive assembly is driven from said start position to said end position.

11. The disposable loading unit of claim 10 further comprising indicia on said housing for cooperating with said firing indicator to assess a travel of said axial drive assembly as said axial drive assembly is driven from said start position to said end position.

12. The disposable loading unit of claim 10 wherein said firing indicator has a color that differs from a color of said housing.

13. A disposable loading unit for attachment to a surgical stapling apparatus, said disposable loading unit comprising:
    a staple cartridge supported in a carrier operably couplable to the surgical stapling apparatus;
    an anvil assembly movably coupled to said carrier for selective movable travel between open and closed positions relative to said staple cartridge;
    an axial drive assembly having a distal end portion constructed to move in a distal direction from a start position to an end position through said staple cartridge in response to a drive motion imparted to said axial drive assembly from the surgical stapling apparatus; and
    a firing indicator movably supported on said anvil assembly for contact by a portion of said axial drive assembly as said axial drive assembly is driven from said start position to said end position.

14. The disposable loading unit of claim 13 wherein said anvil assembly comprises and anvil portion and a cover portion attached to said anvil portion and wherein said firing indicator is slidably mounted on said anvil cover.

15. The disposable loading unit of claim 13 wherein said firing indicator is movably supported in an elongated slot in said anvil assembly.

16. The disposable loading unit of claim 13 further comprising indicia on said anvil assembly to assess a travel of said axial drive assembly as said axial drive assembly is driven from said start position to said end position.

17. The disposable loading unit of claim 13 further comprising another firing indicator assembly associated with said carrier.

* * * * *